United States Patent
Bullivant et al.

(10) Patent No.: US 6,277,114 B1
(45) Date of Patent: Aug. 21, 2001

(54) ELECTRODE ASSEMBLY FOR AN ELECTROSURICAL INSTRUMENT

(75) Inventors: Jarrett Bullivant, Llanblethian; Robert William Goddard, Pontypridd, both of (GB)

(73) Assignee: Gyrus Medical Limited, Cardiff (GB)

(*) Notice: Subject to any disclaimer, the term of this patent is extended or adjusted under 35 U.S.C. 154(b) by 0 days.

(21) Appl. No.: 09/271,916

(22) Filed: Mar. 18, 1999

(Under 37 CFR 1.47)

(30) Foreign Application Priority Data

Apr. 3, 1998 (GB) .................................... 9807303

(51) Int. Cl.[7] .................................... A61B 18/18
(52) U.S. Cl. .................. 606/41; 606/48; 606/50
(58) Field of Search ................. 606/41, 46, 47, 606/48, 49, 50

(56) References Cited

U.S. PATENT DOCUMENTS

| Re. 31,990 | * 9/1985 | Sluetz et al. ................ 607/38 |
|---|---|---|
| Re. 33,925 | 5/1992 | Bales et al. . |
| 164,184 | 6/1875 | Kidder . |

(List continued on next page.)

FOREIGN PATENT DOCUMENTS

| 243478 | 7/1946 | (CH) . |
|---|---|---|
| 651428 | 9/1937 | (DE) . |
| 949370 | 3/1956 | (DE) . |

(List continued on next page.)

OTHER PUBLICATIONS

Cook, Albert M. & John G. Webster, *Therapeutic Medical Devices Application and Design*, Prentice–Hall Inc., New Jersey, 1982, p. 349.
Pearce, John A., *Electrosurgery*, John Wiley & Sons Inc., New York, 1986, pp. 17, 69–75 and 87.
Wyeth, G.A., *Electrosurgical Unit*, pp. 1180–1202.
Everest Medical Technologies, Inc., "Everest Bipolar Laparoscopic Cholecystectomy," Transcript of Lecture by Dr. Olsen, Oct. 7, 1991.

(List continued on next page.)

*Primary Examiner*—Linda C. M. Dvorak
*Assistant Examiner*—R. Kearney
(74) *Attorney, Agent, or Firm*—Nixon & Vanderhye P.C.

(57) ABSTRACT

An electrode assembly for electrosurgical removal of tissue immersed in an electrically conductive liquid has an elongate support structure including at least a pair of wire conductors for carrying radio frequency current, and a bipolar electrode assembly, extending transversely between the two conductors. The tip assembly has a ribbed transversely extending active electrode and a smooth-surfaced transversely extending return electrode mounted on opposite faces of a ceramic insulator body. The electrodes comprise metallic plates on the insulator body, the surface area of the active electrode being between 1.25 to 2 times that of the return electrode. To provide for endoscope mounting, the wire conductors are secured to a spring chip for detachable mounting to the telescope tube of an endoscope.

33 Claims, 6 Drawing Sheets

U.S. PATENT DOCUMENTS

| | | |
|---|---|---|
| 1,366,756 | 1/1921 | Wappler . |
| 1,735,271 | 11/1929 | Groff . |
| 1,814,791 | 7/1931 | Ende . |
| 1,889,609 | 11/1932 | Mutscheller . |
| 1,932,258 | 10/1933 | Wappler . |
| 1,943,543 | 1/1934 | McFadden . |
| 1,952,617 | 3/1934 | Wappler . |
| 1,983,669 | 12/1934 | Kimble . |
| 2,050,904 | 8/1936 | Trice . |
| 2,056,377 | 10/1936 | Wappler . |
| 2,196,171 | 4/1940 | Arnesen . |
| 2,888,928 | 6/1959 | Seiger . |
| 3,035,580 | 5/1962 | Guiorguiev . |
| 3,460,539 | 8/1969 | Anhalt, Sr. . |
| 3,595,239 | 7/1971 | Petersen . |
| 3,601,126 | 8/1971 | Estes . |
| 3,614,414 | 10/1971 | Gores . |
| 3,648,001 | 3/1972 | Anderson et al. . |
| 3,685,518 | 8/1972 | Beurle et al. . |
| 3,699,967 | 10/1972 | Anderson . |
| 3,707,149 | 12/1972 | Hao et al. . |
| 3,801,766 | 4/1974 | Morrison et al. . |
| 3,815,604 | 6/1974 | O'Malley et al. . |
| 3,845,771 | 11/1974 | Vise . |
| 3,847,153 | 11/1974 | Weissman . |
| 3,870,047 | 3/1975 | Gonser . |
| 3,885,569 | 5/1975 | Judson . |
| 3,898,991 | 8/1975 | Ikuno et al. . |
| 3,901,242 | 8/1975 | Storz . |
| 3,902,494 | 9/1975 | Haberlen et al. . |
| 3,903,891 | 9/1975 | Brayshaw . |
| 3,920,021 | 11/1975 | Hiltebrandt . |
| 3,920,022 | 11/1975 | Pastor . |
| 3,923,063 | 12/1975 | Andrews et al. . |
| 3,929,137 | 12/1975 | Gonser et al. . |
| 3,939,839 | 2/1976 | Curtiss . |
| 3,945,375 | 3/1976 | Banko . |
| 3,963,030 | 6/1976 | Newton . |
| 3,964,487 | 6/1976 | Judson . |
| 3,970,088 | 7/1976 | Morrison . |
| 3,974,833 | 8/1976 | Durden, III . |
| 4,011,872 | 3/1977 | Komiya . |
| 4,016,881 | 4/1977 | Rioux et al. . |
| 4,024,467 | 5/1977 | Andrews et al. . |
| 4,033,351 | 7/1977 | Hetzel . |
| 4,040,426 | 8/1977 | Morrison, Jr. . |
| 4,043,342 | 8/1977 | Morrison, Jr. . |
| 4,051,855 | 10/1977 | Schneiderman . |
| 4,060,088 | 11/1977 | Morrison, Jr. et al. . |
| 4,069,827 | 1/1978 | Dominy . |
| 4,074,718 | 2/1978 | Morrison, Jr. . |
| 4,092,986 | 6/1978 | Schneiderman . |
| 4,114,623 | 9/1978 | Meinke et al. . |
| 4,116,198 | 9/1978 | Roos . |
| 4,119,102 | 10/1978 | LeVeen . |
| 4,126,137 | 11/1978 | Archibald . |
| 4,154,240 | 5/1979 | Ikuno et al. . |
| 4,189,685 | 2/1980 | Doss . |
| 4,200,104 | 4/1980 | Harris . |
| 4,202,337 | 5/1980 | Hren et al. . |
| 4,204,549 | 5/1980 | Paglione . |
| 4,210,152 | 7/1980 | Berry . |
| 4,228,800 | 10/1980 | Degler, Jr. et al. . |
| 4,248,231 | 2/1981 | Herczog et al. . |
| 4,271,837 | 6/1981 | Schuller . |
| 4,281,373 | 7/1981 | Mabille . |
| 4,301,802 | 11/1981 | Poler . |
| 4,326,529 | 4/1982 | Doss et al. . |
| 4,346,332 | 8/1982 | Walden . |
| 4,376,263 | 3/1983 | Pittroff et al. . |
| 4,381,007 | 4/1983 | Doss . |
| 4,416,277 | 11/1983 | Newton et al. . |
| 4,418,692 | 12/1983 | Guay . |
| 4,429,698 | 2/1984 | Bentall . |
| 4,448,198 | 5/1984 | Turner . |
| 4,474,179 | 10/1984 | Koch . |
| 4,476,862 | 10/1984 | Pao . |
| 4,492,231 | 1/1985 | Auth . |
| 4,494,541 | 1/1985 | Archibald . |
| 4,512,338 | 4/1985 | Balko et al. . |
| 4,517,976 | 5/1985 | Murakoshi et al. . |
| 4,524,770 | 6/1985 | Orandi . |
| 4,532,924 | 8/1985 | Auth et al. . |
| 4,534,347 | 8/1985 | Taylor . |
| 4,548,207 | 10/1985 | Reimels . |
| 4,559,943 | 12/1985 | Bowers . |
| 4,559,951 | 12/1985 | Dahl et al. . |
| 4,562,838 | 1/1986 | Walker . |
| 4,565,200 | 1/1986 | Cosman . |
| 4,567,890 | 2/1986 | Ohta et al. . |
| 4,580,557 | 4/1986 | Hertzmann . |
| 4,590,934 | 5/1986 | Malis et al. . |
| 4,593,691 | 6/1986 | Lindstrom et al. . |
| 4,617,927 | 10/1986 | Manes . |
| 4,657,015 | 4/1987 | Irnich . |
| 4,658,819 | 4/1987 | Harris et al. . |
| 4,658,820 | 4/1987 | Klicek . |
| 4,669,468 | 6/1987 | Cartmell et al. . |
| 4,674,499 | 6/1987 | Pao . |
| 4,681,122 | 7/1987 | Winters et al. . |
| 4,682,596 | 7/1987 | Bales et al. . |
| 4,688,569 | 8/1987 | Rabinowitz . |
| 4,696,668 | 9/1987 | Wilcox . |
| 4,706,667 | 11/1987 | Roos . |
| 4,709,698 | 12/1987 | Johnston et al. . |
| 4,712,544 | 12/1987 | Ensslin . |
| 4,727,874 | 3/1988 | Bowers et al. . |
| 4,735,201 | 4/1988 | O'Reilly . |
| 4,739,759 | 4/1988 | Rexroth et al. . |
| 4,762,603 * | 8/1988 | Morin ................................. 204/279 |
| 4,769,005 | 9/1988 | Ginsburg et al. . |
| 4,781,175 | 11/1988 | McGreevy et al. . |
| 4,799,480 | 1/1989 | Abraham et al. . |
| 4,800,899 | 1/1989 | Elliott . |
| 4,802,476 | 2/1989 | Noerenberg et al. . |
| 4,805,616 | 2/1989 | Pao . |
| 4,813,429 | 3/1989 | Eshel et al. . |
| 4,820,298 | 4/1989 | Leveen et al. . |
| 4,823,791 | 4/1989 | D'Amelio et al. . |
| 4,827,927 | 5/1989 | Newton . |
| 4,832,048 | 5/1989 | Cohen . |
| 4,850,353 | 7/1989 | Stasz et al. . |
| 4,860,744 | 8/1989 | Johnson et al. . |
| 4,878,493 | 11/1989 | Pasternak et al. . |
| 4,886,074 | 12/1989 | Bisping . |
| 4,919,129 | 4/1990 | Weber, Jr. et al. . |
| 4,920,978 | 5/1990 | Colvin . |
| 4,931,047 | 6/1990 | Broadwin et al. . |
| 4,936,281 | 6/1990 | Stasz . |
| 4,936,301 | 6/1990 | Rexroth et al. . |
| 4,936,310 | 6/1990 | Engstrom et al. . |
| 4,936,842 | 6/1990 | D'Amelio et al. . |
| 4,943,290 | 7/1990 | Rexroth et al. . |
| 4,950,267 | 8/1990 | Ishihara et al. . |
| 4,955,377 | 9/1990 | Lennox et al. . |
| 4,966,597 | 10/1990 | Cosman . |
| 4,967,765 | 11/1990 | Turner et al. . |
| 4,969,885 | 11/1990 | Farin . |
| 4,976,711 | 12/1990 | Parins et al. . |
| 4,994,069 | 2/1991 | Ritchart et al. . |
| 4,998,933 | 3/1991 | Eggers et al. . |

| | | |
|---|---|---|
| 5,007,908 | 4/1991 | Rydell . |
| 5,009,656 | 4/1991 | Reimels . |
| 5,013,312 | 5/1991 | Parins et al. . |
| 5,019,076 | 5/1991 | Yamanashi et al. . |
| 5,035,696 | 7/1991 | Rydell . |
| 5,037,379 | 8/1991 | Clayman et al. . |
| 5,047,026 | 9/1991 | Rydell . |
| 5,047,027 | 9/1991 | Rydell . |
| 5,057,107 | 10/1991 | Parins et al. . |
| 5,062,031 | 10/1991 | Flachenecker et al. . |
| 5,071,418 | 12/1991 | Rosenbaum . |
| 5,080,660 | 1/1992 | Buelna . |
| 5,083,565 | 1/1992 | Parins . |
| 5,085,659 | 2/1992 | Rydell . |
| 5,088,997 | 2/1992 | Delahuerga et al. . |
| 5,098,431 | 3/1992 | Rydell . |
| 5,099,840 | 3/1992 | Goble et al. . |
| 5,108,391 | 4/1992 | Flachenecker et al. . |
| 5,108,407 | 4/1992 | Geremia et al. . |
| 5,117,978 | 6/1992 | Blumenfeld et al. . |
| 5,122,138 | 6/1992 | Manwaring . |
| 5,133,365 | 7/1992 | Heil, Jr. et al. . |
| 5,158,561 | 10/1992 | Rydell et al. . |
| 5,167,658 | 12/1992 | Ensslin . |
| 5,167,659 | 12/1992 | Ohtomo et al. . |
| 5,171,255 | 12/1992 | Rydell . |
| 5,171,311 | 12/1992 | Rydell et al. . |
| 5,178,620 | 1/1993 | Eggers et al. . |
| 5,190,517 | 3/1993 | Zieve et al. . |
| 5,195,959 | 3/1993 | Smith . |
| 5,196,007 | 3/1993 | Ellman et al. . |
| 5,197,963 | 3/1993 | Parins . |
| 5,201,743 | 4/1993 | Haber et al. . |
| 5,207,675 | 5/1993 | Canady . |
| 5,211,625 | 5/1993 | Sakurai et al. . |
| 5,217,457 | 6/1993 | Delahuerga et al. . |
| 5,217,458 | 6/1993 | Parins . |
| 5,217,459 | 6/1993 | Kamerling . |
| 5,221,281 | 6/1993 | Klicek . |
| 5,244,462 | 9/1993 | Delahuerga et al. . |
| 5,249,585 | 10/1993 | Turner et al. . |
| 5,250,047 | 10/1993 | Rydell . |
| 5,257,990 | 11/1993 | Nash . |
| 5,258,006 | 11/1993 | Rydell et al. . |
| 5,259,395 | 11/1993 | Li . |
| 5,261,906 | 11/1993 | Pennino et al. . |
| 5,267,994 | 12/1993 | Gentelia et al. . |
| 5,267,997 | 12/1993 | Farin et al. . |
| 5,277,201 | 1/1994 | Stern . |
| 5,277,696 | 1/1994 | Hagen . |
| 5,281,213 | 1/1994 | Milder et al. . |
| 5,281,216 | 1/1994 | Klicek . |
| 5,282,799 | 2/1994 | Rydell . |
| 5,282,845 | 2/1994 | Bush et al. . |
| 5,290,282 | 3/1994 | Casscells . |
| 5,290,283 | 3/1994 | Suda . |
| 5,300,068 | 4/1994 | Rosar et al. . |
| 5,300,069 | 4/1994 | Hunsberger et al. . |
| 5,300,070 | 4/1994 | Gentelia et al. . |
| 5,304,214 | 4/1994 | DeFord et al. . |
| 5,306,238 | 4/1994 | Fleenor . |
| 5,317,155 | 5/1994 | King . |
| 5,318,563 | 6/1994 | Malis et al. . |
| 5,320,627 | 6/1994 | Sorensen et al. . |
| 5,330,470 | 7/1994 | Hagen . |
| 5,330,471 | 7/1994 | Eggers . |
| 5,334,193 | 8/1994 | Nardella . |
| 5,334,198 | 8/1994 | Hart et al. . |
| 5,336,222 | 8/1994 | Durgin, Jr. et al. . |
| 5,342,357 | 8/1994 | Nardella . |
| 5,342,391 | 8/1994 | Foshee et al. . |
| 5,344,428 | 9/1994 | Griffiths . |
| 5,352,222 | 10/1994 | Rydell . |
| 5,354,296 | 10/1994 | Turkel . |
| 5,366,443 | 11/1994 | Eggers et al. . |
| 5,370,645 | 12/1994 | Klicek et al. . |
| 5,370,675 | 12/1994 | Edwards et al. . |
| 5,372,596 | 12/1994 | Klicek et al. . |
| 5,382,247 | 1/1995 | Cimino et al. . |
| 5,383,874 | 1/1995 | Jackson et al. . |
| 5,383,876 | 1/1995 | Nardella . |
| 5,383,917 | 1/1995 | Desai et al. . |
| 5,383,923 | 1/1995 | Webster, Jr. . |
| 5,395,363 | 3/1995 | Billings et al. . |
| 5,395,368 | 3/1995 | Ellman et al. . |
| 5,403,311 | 4/1995 | Abele et al. . |
| 5,419,767 | 5/1995 | Eggers et al. . |
| 5,422,567 | 6/1995 | Matsunaga . |
| 5,423,808 | 6/1995 | Edwards et al. . |
| 5,423,809 | 6/1995 | Klicek . |
| 5,423,810 | 6/1995 | Goble et al. . |
| 5,423,811 | 6/1995 | Imran et al. . |
| 5,431,649 | 7/1995 | Mulier et al. . |
| 5,437,662 | 8/1995 | Nardella . |
| 5,438,302 | 8/1995 | Goble . |
| 5,441,499 | 8/1995 | Fritzsch . |
| 5,443,470 | 8/1995 | Stern et al. . |
| 5,454,809 | 10/1995 | Janssen . |
| 5,462,521 | 10/1995 | Brucker et al. . |
| 5,472,441 | 12/1995 | Edwards et al. . |
| 5,472,443 | 12/1995 | Cordis et al. . |
| 5,480,397 | 1/1996 | Eggers et al. . |
| 5,480,398 | 1/1996 | Eggers et al. . |
| 5,496,312 | 3/1996 | Klicek . |
| 5,496,314 | 3/1996 | Eggers . |
| 5,505,728 | 4/1996 | Ellman et al. . |
| 5,505,730 | 4/1996 | Edwards . |
| 5,507,743 | 4/1996 | Edwards et al. . |
| 5,514,129 | 5/1996 | Smith . |
| 5,514,130 | 5/1996 | Baker . |
| 5,514,131 | 5/1996 | Edwards et al. . |
| 5,520,684 | 5/1996 | Imran . |
| 5,520,685 | 5/1996 | Wojciechowicz . |
| 5,522,815 | 6/1996 | Durgin, Jr. et al. . |
| 5,527,331 | 6/1996 | Kresch et al. . |
| 5,531,744 | 7/1996 | Nardella et al. . |
| 5,536,267 | 7/1996 | Edwards et al. . |
| 5,540,680 | 7/1996 | Guglielmi et al. . |
| 5,540,681 | 7/1996 | Strul et al. . |
| 5,540,682 | 7/1996 | Gardner et al. . |
| 5,540,683 | 7/1996 | Ichikawa et al. . |
| 5,540,684 | 7/1996 | Hassler, Jr. . |
| 5,540,685 | 7/1996 | Parins et al. . |
| 5,542,916 | 8/1996 | Hirsch et al. . |
| 5,542,945 | 8/1996 | Fritzsch . |
| 5,545,161 | 8/1996 | Imran . |
| 5,545,193 | 8/1996 | Fleischman et al. . |
| 5,549,605 | 8/1996 | Hahnen . |
| 5,554,172 | 9/1996 | Horner et al. . |
| 5,555,618 | 9/1996 | Winkel . |
| 5,556,396 | 9/1996 | Cohen et al. . |
| 5,556,397 | 9/1996 | Long et al. . |
| 5,558,671 | 9/1996 | Yates . |
| 5,562,720 | 10/1996 | Stern et al. . |
| 5,569,164 | 10/1996 | Lurz . |
| 5,569,242 | 10/1996 | Lax et al. . |
| 5,569,244 | 10/1996 | Hahnen . |
| 5,569,245 | 10/1996 | Guglielmi et al. . |
| 5,571,100 | 11/1996 | Goble et al. . |
| 5,575,789 | 11/1996 | Bell et al. . |
| 5,578,007 | 11/1996 | Imran . |
| 5,582,609 | 12/1996 | Swanson et al. . |

| | | |
|---|---|---|
| 5,582,610 | 12/1996 | Grossi et al. . |
| 5,584,830 | 12/1996 | Ladd et al. . |
| 5,591,141 | 1/1997 | Nettekoven . |
| 5,599,344 | 2/1997 | Paterson . |
| 5,599,345 | 2/1997 | Edwards et al. . |
| 5,599,346 | 2/1997 | Edwards et al. . |
| 5,599,347 | 2/1997 | Hart et al. . |
| 5,599,348 | 2/1997 | Gentelia et al. . |
| 5,599,349 | 2/1997 | D'Amelio . |
| 5,603,711 | 2/1997 | Parins et al. . |
| 5,603,712 | 2/1997 | Koranda et al. . |
| 5,607,422 | 3/1997 | Smeets et al. . |
| 5,609,151 | 3/1997 | Mulier et al. . |
| 5,609,573 | 3/1997 | Sandock . |
| 5,611,798 | 3/1997 | Eggers . |
| 5,620,481 | 4/1997 | Desai et al. . |
| 5,624,439 | 4/1997 | Edwards et al. . |
| 5,626,560 | 5/1997 | Soring . |
| 5,626,575 | 5/1997 | Crenner . |
| 5,626,576 | 5/1997 | Janssen . |
| 5,626,578 | 5/1997 | Tihon . |
| 5,628,745 | 5/1997 | Bek . |
| 5,628,771 | 5/1997 | Mizukawa et al. . |
| 5,630,426 | 5/1997 | Eggers et al. . |
| 5,633,578 | 5/1997 | Eggers et al. . |
| 5,634,924 * | 6/1997 | Turkel et al. .......................... 606/46 |
| 5,647,869 | 7/1997 | Goble et al. . |
| 5,672,174 | 9/1997 | Gough et al. . |
| 5,683,366 | 11/1997 | Eggers et al. . |
| 5,693,045 | 12/1997 | Eggers . |
| 5,697,281 | 12/1997 | Eggers et al. . |
| 5,697,536 | 12/1997 | Eggers et al. . |
| 5,697,882 | 12/1997 | Eggers et al. . |
| 5,697,909 | 12/1997 | Eggers et al. . |
| 5,700,262 | 12/1997 | Acosta et al. . |
| 5,725,524 | 3/1998 | Mulier et al. . |
| 5,735,846 | 4/1998 | Panescu et al. . |
| 5,766,153 | 6/1998 | Eggers et al. . |
| 5,779,700 * | 7/1998 | Hahnen et al. ........................ 606/46 |
| 5,810,764 | 9/1998 | Eggers et al. . |
| 5,810,809 | 9/1998 | Rydell . |
| 5,830,214 | 11/1998 | Flom et al. . |
| 5,833,689 | 11/1998 | Long . |
| 5,843,019 | 12/1998 | Eggers et al. . |
| 5,860,951 | 1/1999 | Eggers et al. . |
| 5,871,469 | 2/1999 | Eggers et al. . |
| 5,873,855 | 2/1999 | Eggers et al. . |
| 5,888,198 | 3/1999 | Eggers et al. . |
| 5,891,095 | 4/1999 | Eggers et al. . |
| 5,902,272 | 5/1999 | Eggers et al. . |
| 5,904,681 | 5/1999 | West, Jr. . |
| 5,919,191 * | 7/1999 | Lennox et al. ........................ 606/48 |
| 5,941,876 | 8/1999 | Nardella et al. . |
| 5,944,715 | 8/1999 | Goble et al. . |
| 6,004,319 | 12/1999 | Goble et al. . |
| 6,013,076 | 1/2000 | Goble et al. . |
| 6,015,406 | 1/2000 | Goble et al. . |
| 6,027,501 | 2/2000 | Goble et al. . |
| 6,056,746 | 5/2000 | Goble et al. . |
| 6,090,106 | 7/2000 | Goble et al. . |
| 6,093,186 | 7/2000 | Goble . |
| 6,174,308 | 1/2001 | Goble et al. . |
| 6,197,025 | 3/2001 | Grossi et al. . |

FOREIGN PATENT DOCUMENTS

| | | |
|---|---|---|
| 1007960 | 5/1957 | (DE) . |
| 2222820 | 11/1973 | (DE) . |
| 2457900 | 5/1976 | (DE) . |
| 2930982 | 2/1981 | (DE) . |
| 3209444 | 10/1982 | (DE) . |
| 3215832A | 11/1982 | (DE) . |
| 3119735 | 1/1983 | (DE) . |
| 3245570 | 6/1984 | (DE) . |
| 222207 | 5/1985 | (DE) . |
| 3423356 | 1/1986 | (DE) . |
| 3427517 | 1/1986 | (DE) . |
| 3511107 | 10/1986 | (DE) . |
| 3623688 | 1/1987 | (DE) . |
| 3530335 | 3/1987 | (DE) . |
| 3707820 | 9/1987 | (DE) . |
| 3622337 C2 | 1/1988 | (DE) . |
| 3642077 C2 | 6/1988 | (DE) . |
| 3708801 C2 | 9/1988 | (DE) . |
| 3824913 | 2/1990 | (DE) . |
| 3838840 C2 | 5/1990 | (DE) . |
| 3930451 | 3/1991 | (DE) . |
| 4108269 C2 | 6/1992 | (DE) . |
| 4103972 C2 | 8/1992 | (DE) . |
| 4126608 | 2/1993 | (DE) . |
| 4139029 C2 | 6/1993 | (DE) . |
| 4217999 A1 | 12/1993 | (DE) . |
| 4237321 A1 | 5/1994 | (DE) . |
| 4323585 | 1/1995 | (DE) . |
| 4339049 | 5/1995 | (DE) . |
| 4425015 | 1/1996 | (DE) . |
| 19530004 | 3/1996 | (DE) . |
| 4429478 | 3/1996 | (DE) . |
| 19510185 | 10/1996 | (DE) . |
| 19512640 C2 | 10/1996 | (DE) . |
| 19514552 | 10/1996 | (DE) . |
| 19514553 C1 | 10/1996 | (DE) . |
| 19526243 C1 | 1/1997 | (DE) . |
| 19526244 | 1/1997 | (DE) . |
| 19543547 C1 | 1/1997 | (DE) . |
| 29617461 | 1/1997 | (DE) . |
| 19630601 | 2/1997 | (DE) . |
| 19537897 | 3/1997 | (DE) . |
| 19542417 | 5/1997 | (DE) . |
| 19542418 | 5/1997 | (DE) . |
| 19542419 | 5/1997 | (DE) . |
| 19545539 | 6/1997 | (DE) . |
| 19545756 | 6/1997 | (DE) . |
| 19650797 | 6/1997 | (DE) . |
| 0 013605 | 7/1980 | (EP) . |
| 0 049633 | 4/1982 | (EP) . |
| 0 067680 | 12/1982 | (EP) . |
| 0 136855 | 4/1985 | (EP) . |
| 0 219568 | 12/1985 | (EP) . |
| 0 205851 | 12/1986 | (EP) . |
| 0 280798A | 9/1988 | (EP) . |
| 0 310431 | 4/1989 | (EP) . |
| 0 316469 | 5/1989 | (EP) . |
| 0 325456 | 7/1989 | (EP) . |
| 0 332308 | 9/1989 | (EP) . |
| 0 373670 | 6/1990 | (EP) . |
| 0 392837 | 10/1990 | (EP) . |
| 0 407057 | 1/1991 | (EP) . |
| 0 412426 | 2/1991 | (EP) . |
| 0 437377 | 7/1991 | (EP) . |
| 0 448798 | 10/1991 | (EP) . |
| 0 499491 | 8/1992 | (EP) . |
| 0 507622 | 10/1992 | (EP) . |
| 0 509670 | 10/1992 | (EP) . |
| 0 517243 | 12/1992 | (EP) . |
| 0 518230 | 12/1992 | (EP) . |
| 0 530400 | 3/1993 | (EP) . |
| 0 536440 | 4/1993 | (EP) . |
| 0 558316 | 9/1993 | (EP) . |
| 0 558318 | 9/1993 | (EP) . |
| 0 647435 | 4/1995 | (EP) . |
| 0 653192 | 5/1995 | (EP) . |
| 0 674909 | 10/1995 | (EP) . |

| | | | | | |
|---|---|---|---|---|---|
| 0 684015 | 11/1995 | (EP). | WO 95/25472 | 9/1995 | (WO). |
| 0 688536 | 12/1995 | (EP). | WO 95/26686 | 10/1995 | (WO). |
| 0 692224 | 1/1996 | (EP). | WO 95/30377 | 11/1995 | (WO). |
| 0 694290 | 1/1996 | (EP). | WO 95/31144 | 11/1995 | (WO). |
| 0 697199 | 2/1996 | (EP). | WO 96/00036 | 1/1996 | (WO). |
| 0 709065 | 5/1996 | (EP). | WO 96/00039 | 1/1996 | (WO). |
| 0 714635 | 6/1996 | (EP). | WO 96/00040 | 1/1996 | (WO). |
| 0 717967 | 6/1996 | (EP). | WO 96/00042 | 1/1996 | (WO). |
| 0 732080 | 9/1996 | (EP). | WO 96/00043 | 1/1996 | (WO). |
| 0 733345 | 9/1996 | (EP). | WO 96/00528 | 1/1996 | (WO). |
| 0 737447 | 10/1996 | (EP). | WO 96/04859 | 2/1996 | (WO). |
| 0 740926 | 11/1996 | (EP). | WO 96/07360 | 3/1996 | (WO). |
| 0 754437 | 1/1997 | (EP). | WO 96/09010 | 3/1996 | (WO). |
| 57862 | 9/1953 | (FR). | WO 96/10367 | 4/1996 | (WO). |
| 1215305 | 4/1960 | (FR). | WO 96/11638 | 4/1996 | (WO). |
| 1454773 | 10/1966 | (FR). | WO 96/14020 | 5/1996 | (WO). |
| 2313949 | 1/1977 | (FR). | WO 96/14021 | 5/1996 | (WO). |
| 2443829 | 7/1980 | (FR). | WO 96/18349 | 6/1996 | (WO). |
| 2501034 | 9/1982 | (FR). | WO 96/19152 | 6/1996 | (WO). |
| 2645008 | 10/1990 | (FR). | WO 96/23448 | 8/1996 | (WO). |
| 1361497 | 7/1974 | (GB). | WO 96/23449 | 8/1996 | (WO). |
| 2037167 | 7/1980 | (GB). | WO 96/24296 | 8/1996 | (WO). |
| 1583397 | 1/1981 | (GB). | WO 96/24301 | 8/1996 | (WO). |
| 2084880 | 4/1982 | (GB). | WO 96/27337 | 9/1996 | (WO). |
| 2101893 | 1/1983 | (GB). | WO 96/29946 | 10/1996 | (WO). |
| 2133290 | 7/1984 | (GB). | WO 96/32897 | 10/1996 | (WO). |
| 2145932 | 4/1985 | (GB). | WO 96/34567 | 11/1996 | (WO). |
| 2161081 | 1/1986 | (GB). | WO 96/34569 | 11/1996 | (WO). |
| 2164473 | 3/1986 | (GB). | WO 96/34570 | 11/1996 | (WO). |
| 2165761 | 4/1986 | (GB). | WO 96/34571 | 11/1996 | (WO). |
| 2177309 | 1/1987 | (GB). | WO 96/37146 | 11/1996 | (WO). |
| 2179861 | 3/1987 | (GB). | WO 96/38094 | 12/1996 | (WO). |
| 2213381 | 8/1989 | (GB). | WO 96/39085 | 12/1996 | (WO). |
| 2214430 | 9/1989 | (GB). | WO 96/39086 | 12/1996 | (WO). |
| 2269538 | 2/1994 | (GB). | WO 96/39088 | 12/1996 | (WO). |
| 62-211060 | 9/1987 | (JP). | WO 96/39089 | 12/1996 | (WO). |
| 644491 | 1/1979 | (RU). | WO 96/39966 | 12/1996 | (WO). |
| WO 81/03271 | 11/1981 | (WO). | WO 96/39967 | 12/1996 | (WO). |
| WO 82/00084 | 1/1982 | (WO). | WO 97/00646 | 1/1997 | (WO). |
| WO 82/02488 | 8/1982 | (WO). | WO 97/00647 | 1/1997 | (WO). |
| WO 84/03829 | 10/1984 | (WO). | PCT/GB97/ 00066 | 5/1997 | (WO). |
| WO 88/01851 | 3/1988 | (WO). | WO 97/24993 | 7/1997 | (WO). |
| WO 90/03152 | 4/1990 | (WO). | WO 97/24994 | 7/1997 | (WO). |
| WO 93/08756 | 5/1993 | (WO). | WO 97/38637 | 10/1997 | (WO). |
| WO 93/13718 | 7/1993 | (WO). | WO 98/00070 | 1/1998 | (WO). |
| WO 93/13816 | 7/1993 | (WO). | WO 98/14131 | 4/1998 | (WO). |
| WO 93/16650 | 9/1993 | (WO). | | | |
| WO 93/19681 | 10/1993 | (WO). | | | |
| WO 93/19682 | 10/1993 | (WO). | | | |
| WO 93/20747 | 10/1993 | (WO). | | | |
| WO 93/20877 | 10/1993 | (WO). | | | |
| WO 94/04220 | 3/1994 | (WO). | | | |
| WO 94/06510 | 3/1994 | (WO). | | | |
| WO 94/10921 | 5/1994 | (WO). | | | |
| WO 94/10924 | 5/1994 | (WO). | | | |
| WO 94/10925 | 5/1994 | (WO). | | | |
| WO 94/23659 | 10/1994 | (WO). | | | |
| WO 94/26228 | 11/1994 | (WO). | | | |
| WO 94/28809 | 12/1994 | (WO). | | | |
| WO 95/02369 | 1/1995 | (WO). | | | |
| WO 95/05781 | 3/1995 | (WO). | | | |
| WO 95/09576 | 4/1995 | (WO). | | | |
| WO 95/09577 | 4/1995 | (WO). | | | |
| WO 95/10320 | 4/1995 | (WO). | | | |
| WO 95/10321 | 4/1995 | (WO). | | | |
| WO 95/17855 | 7/1995 | (WO). | | | |
| WO 95/18575 | 7/1995 | (WO). | | | |
| WO 95/19733 | 7/1995 | (WO). | | | |
| WO 95/20360 | 8/1995 | (WO). | | | |
| WO 95/23558 | 9/1995 | (WO). | | | |
| WO 95/24160 | 9/1995 | (WO). | | | |

OTHER PUBLICATIONS

Dobbie, A.K., "The Electrical Aspects of Surgical Diathermy," Biomedical Engineering, May 1969, pp. 206–216.

Valleylab, Excerpts from Valleylab SSE2L Instruction Manual, Valleylab Part No. A 945 110 005 H, Jan. 6, 1983.

Schurr, M. O. et al., "Histologic Effects of Different Technologies for Dissection in Endoscopic Surgery:Nd:YAG Laser, High Frequency and Water–Jet," End. Surg., vol. 2, 1994, pp. 195–201.

Newman, Laura, "Could Twist on TURP Knock Lasers Out," Urology Times, vol. 3, No. 3, Mar. 1995, p. 21.

ArthroCare Corporation, "The Arthrocare Arthroscopic System," 1995.

Tucker, R.D. et al., "In Vivo Effect of 5 French Bipolar and Monopolar Electro–Surgical Probes on Porcine Bladder," Urological Research, Springer–Verlag 1990, 18:291–294.

Kramolowsky, Eugene V. et al., "The Urological Application of Electrosurgery," The Journal of Urology, vol. 146, Sep. 1991, pp. 669–674.

Tucker, Robert D. et al., "A Comparison of Urologic Application of Bipolar Versus Monopolar Five French Electrosurgical Probes," The Journal of Urology, vol. 141, Mar. 1989, pp. 662–665.

Kramolowsky, Eugene V. et al., "Use of 5F Bipolar Electrosurgical Probe in Endoscopic Urological Procedures," The Journal of Urology, vol. 143, Feb. 1990, pp. 275–277.

Tucker, Robert et al., "A Bipolar Electrosurgical TURP Loop, "Abstract of Paper P14–11, 7$^{th}$ World Congress on Endourology and ESWL, Nov. 27–30, Kyoto, Japan, 1989, p. 248.

Ramsay, J.W. A. et al., "A Comparison of Bipolar and Monopolar Diathermy Probes in Experimental Animals," Urological Research, Springer–Verlag 1985, 13:99–102.

German Article w/Translation: Elsasser, E. and Roos, E., "Concerning an Instrument for Transurethral Resection without Leakage of Current," Medizinal–Marks/Acta Medicotechnica, vol. 24, No. 4, 1976, pp. 129–134.

Nardella, Paul C., "Radio Frequency Energy and Impedance Feedback," SPIE, vol.1068, Catheter–Based Sensing & Imaging Technology, 1989, pp. 42–48.

Honig, William M., "The Mechanism of Cutting in Electrosurgery," IEEE Transactions on Biomedical Engineering, Jan. 1975, pp. 58–65.

Barry, Kevin J. et al., "The Effect of Radiofrequency–Generated Thermal Energy on the Mechanical and Histologic Characteristics of the Arterial Wall In Vivo: Implications for Radiofrequency Angioplasty," American Heart Journal, vol. 117, No. 2, Feb. 1989, pp. 332–341.

Slager, Cornelis J. et al., "Vaporization of Atherosclerotic Plaques by Spark Erosion," Journal of American College of Cardiology, 1985, pp. 1382–1386.

Lee, Benjamin I. et al., "Thermal Compression and Molding of Atherosclerotic Vascular Tissue with Use of Radiofrequency Energy: Implications for Radiofrequency Balloon Angioplasty," Journal of American College of Cardiology, vol. 13, No. 5, Apr. 1989, pp. 1167–1175.

Piercey, J.R.A. et al., "Electrosurgical Treatment of Experimental Bleeding Canine Gastric Ulcers," Gastroenterology, vol. 74, No. 3, 1978, pp. 527–534.

Protell, Robert L. et al., "Computer–Assisted Electrocoagulaton: Bipolar vs. Monopolar in the Treatment of Experimental Canine Gastric Ulcer Bleeding," Gastroenterology, vol. 80, No. 3, 1981, pp. 451–455.

Johnston, James H. et al., "Experimental Comparison of Endoscopic Yttrium–Aluminum–Garnet Laser, Electrosurgery, and Heater Probe for Canine Gut Arterial Coagulation," Gastroenterology, vol. 92, No. 5, May 1987, pp. 1101–1108.

Dennis, M.B. et al., "Evaluation of Electrofulguration in Control of Bleeding of Experimental Gastric Ulcers," Digestive Diseases and Sciences, vol. 24, No. 11, Nov. 1979, pp. 845–848.

Silverstein, Fred E. et al., "Endoscopic Hemostasis Using Laser Photocoagulation and Electrocoagulation," Digestive Diseases and Sciences, vol. 26, No. 7, Jul. Supplement 1981, pp. 31s–40s.

Auth, D.C., "Animal Testing of Endoscopic Hemostasis with Lasers and Other Devices," Endoscopy, vol. 18, Supplement 2, May 1986, pp. 36–39.

McLean, A. J., "The Bovie Electrosurgical Current Generator—Some Underlying Principles and Results," Archives of Surgery, vol. 18, 1929, pp. 1863–1873.

McLean, A. J., "Characteristics of Adequate Electrosurgical Current," American Journal of Surgery, vol. XVIII, No. 3, Feb. 16, 1932, pp. 417–441.

Wattiez, Arnaud et al., *Electrosurgery in Operative Endoscopy*, Blackwell Science Ltd., London, 1995, pp. 87–93, 155–163.

Farin, G., "Pneumatically Controlled Bipolar Cutting Instrument," End. Surg., 1993, pp. 1–3.

Muller, W., "The Advantages of Laparoscopic Assisted Bipolar High–Frequency Surgery," End. Surg., 1993, pp. 1–6.

Reidenbach, H. D., "Fundamentals of Bipolar High–Frequency Surgery," End. Surg. 1993, pp. 85–90.

Penketh, Richard et al., "Clinical Evaluation of the Procision Bipolar Electrosurgical Generator During Laparoscopic Gynaecological Procedures," EAES. 2$^{nd}$ International Congress of the European Association for Endoscopic Surgery, Madrid, Sep. 15–17, 1994.

Lloyd, David M. et al., "A New Portable Bipolar Generator–Use in Laparoscopic Cholecystectomy," EAES, 2$^{nd}$ International Congress of the European Association for Endoscopic Surgery, Madrid, Sep. 15–17, 1994.

Buchelt, Martin et al., "Excimer Laser Ablation of Fibrocartilage: An In Vitro and In Vivo Study," Lasers in Surgery and Medicine, vol. 11, 1991, pp. 271–279.

Srinivasan, R., "Ablation of Polymers and Biological Tissue by Ultraviolent Lasers," Science, vol. 234, Oct. 31, 1986, pp. 559–565.

Pearce, John A., "Chapter 3 Electrosurgery," *Handbook of Biomedical Engineering*, Ed. Jacob Kline, Academic Press, Inc., 1988, pp. 99–113.

Selikowitz, Stuart M. et al., "Electric Current and Voltage Recordings on the Myocardium During Electrosurgical Procedures in Canines," *Reprint form Surgery, Gynecology & Obstetrics*, Mar. 1987, vol. 164, pp. 219–224.

Tucker, Robert D. et al., "Demodulated Low Frequency Currents form Electrosurgical Procedures," Surgery, Gynecology & Obsterics, Jul. 1984, vol. 159, pp. 39–43.

Lu, David Y. et al., "Electrical Thermal Angioplasty: Catheter Design Features, In Vitro Tissue Ablation Studies and In Vivo Experimental Findings," Am J Cardiol, vol. 60, 1987, pp. 1117–1122.

Malis, Leonard I., "Electrosurgery: Technical Note," J. Neurosurg., vol. 85, 1996, pp. 970–975.

Slager, C. J. et al., "Spark Erosion of Arteriosclerotic Plaques," Kardiologie, vol. 76, Suppl. 6, 1987, pp. 67–71.

Geddes, Leslie A., Medical Device Accidents—With Illustrative Cases, CRC Press, New York, 1998, p. 93(commentary on Honig, William M., "The Mechanism of Cutting in Electrosurgery," IEEE Transactions on Biomedical Engineering, Jan. 1975, pp. 58–65.

Valleylab, Inc., "Force Electrosurgical Generators Instruction Manual," Valleylab Part No. 945 110 039 A, Feb. 1987, pp. 59–62.

Valleylab, Inc., "Advances in Bipolar Electrosurgery for Laparascopic Surgery," Advances in Bipolar Electrosurgery, pp. 1–4.

Description of Codman and Johnson & Johnson Malis CMC–III Bipolar System.

Pfizer/Valleylab Press Release "Valleylab Inc., Introduces The Procision Bipolar Electrosurgery System," Sep. 15, 1994.

ArthroCare Corporation, "ArthroCare Arthroscopic Electrosurgery System, Model 970 Operator's Manual," Feb. 1996.

ArthroCare Corporation,"Arthroscopic Electrosurgery System, System 2000 Operator's Manual," Jan. 1998.

* cited by examiner

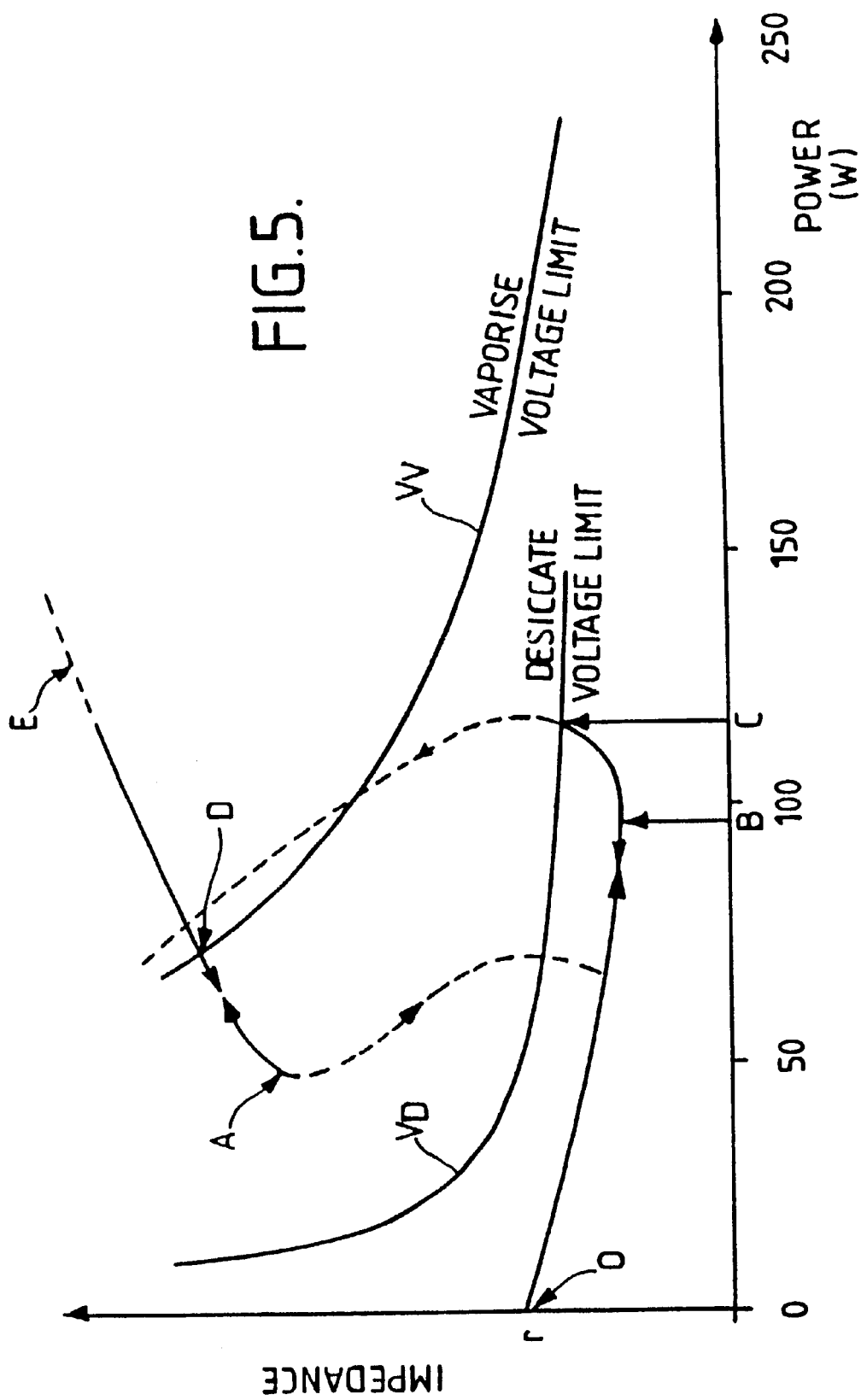

ELECTRODE ASSEMBLY FOR AN ELECTROSURICAL INSTRUMENT

BACKGROUND OF THE INVENTION

This invention relates to an electrode assembly for the electrosurgical removal of tissue immersed in an electrically conductive liquid such as normal saline, and primarily to an electrode assembly for housing in an endoscope, for performing, e.g., transurethral prostatectomy (TURP).

In International Patent Applications Nos. WO 97/00647, WO 97/24994, WO 97/24993, WO 97/00646, WO 97/48345 and WO 97/48346 the applicants disclose a number of bipolar electrode assemblies for mounting on the distal end of the elongate tubular instrument shaft. In each case, the electrode assembly is designed for operation whilst immersed in a conductive liquid, typically normal saline, through which current flows from a tissue treatment electrode placed on or adjacent tissue to be treated, to a return electrode which is spaced back from the tissue treatment electrode away from the tissue surface. An electrosurgical generator suitable for supplying power to the disclosed electrode assemblies is described and shown in the applicant's co-pending European Patent Application No. EP 0754437. This generator provides for different modes of operation, a first mode being a tissue desiccation or coagulation mode in which the peak voltage applied between the electrodes is limited to prevent vapour pocket formation at the tissue treatment electrode, and a second mode in which tissue is vaporised to produce a cutting or bulk removal effect at an operation site. During the second mode the power supplied to the electrode assembly causes the formation, from the conductive liquid, of a vapour pocket around the tissue treatment electrode. In this case, the peak voltage applied to the electrode is limited to control the size of the vapour pocket and to prevent electrode destruction. A third mode of operation is a blended mode achieved by switching between the electrical conditions for the first and second modes.

The full subject matter of the above-mentioned co-pending applications is incorporated in this specification by reference.

The electrode assemblies are typically introduced to a body cavity through the working channel of an endoscope inserted through a natural body orifice or through a separate aperture formed to obtain access to the cavity. In either circumstance, the tubular instrument shaft provides the return path for electrosurgical currents, connection to the tissue treatment electrode being made through an insulated conductor passing through the shaft interior. The tubular member also provides for heat transfer away from the electrodes during operations. Thermal dissipation from the electrodes is enhanced by a portion of the shaft being immersed in the conductive liquid.

Endoscopic urological surgery is performed routinely to treat pathologies of the urinary tract using a range of sophisticated instruments introduced through the urethra. Resectoscopes are a specific form of endoscope originally developed for urological surgery. They have since been used in hysteroscopic and gastrointestinal surgery for removal of soft tissues. Resectoscopes differ from many other endoscopes in that they include an integral trigger mechanism to produce a controlled forwards and backwards motion of an instrument attached to the mechanism. This control is particularly useful during removal of large volumes of tissue and as such, they are the instrument of choice for performing TURP, the removal of benign overgrowth of the prostate gland as well as endometrial and fibroid resection during hysteroscopic surgery and resection of polyps and tumours in the rectum during endoscopic gastrointestinal surgery.

Irrigating solutions may be delivered by continuous or intermittent flow through the resectoscope and may be electrolyte or non-electrolyte based. As the traditional technique for performing TURP is monopolar electrosurgery, a non-electrolyte is most commonly used. Conventional instruments, then, generally comprise a range of monopolar electrodes mounted on the resectoscope. A bipolar instrument is known from U.S. Pat. No. 4,116,198 (Roos). This has a single active electrode in the form of a reciprocable resection loop and a return electrode mounted on the distal end of an instrument shaft. Electrical conduction between the electrodes occurs via a conductive liquid immersing both electrodes.

A resectoscope consists of four main components: an inner sheath, an outer sheath, a telescope and light source assembly, and a working element. The working element, whether passive or active, comprises a reciprocating mechanism mounted on a tube. The tube has a telescope connector at its proximal end and a sealing block located part way along its length, to which the inner sheath connects. The sealing block has a hole through it to allow the telescope to be passed from the proximal to the distal end of the working element, within the bore of the inner sheath. The hole is offset so that the telescope is located in the upper quadrate of the inner sheath aperture to make room for the electrode support tube.

A monopolar electrode supported on a wire-form conductor is inserted through the support tube from the distal end through a second hole in the sealing block. The hole is angled so that the electrode exits the sealing block at an increased distance from the telescope, in order that the electrode passes into the insulation block with sufficient insulating material between the electrode and the telescope to provide electrical isolation. These monopolar electrodes are typically of a wire shaft construction to facilitate introduction through the resectoscope with a large working tip of a wire loop or roller ball configuration. A roller electrode is disclosed in U.S. Pat. No. 5,599,349 (D'Amelio).

It can be advantageous to use an electrode supported by wires with conventional endoscopes, the electrode being loaded in the working channel from distal end to proximal end as opposed to conventional loading from proximal end to distal end. The latter loading technique limits the dimension of the working tip of the electrode to the internal diameter of the working channel.

Additionally, wire-form support to an electrode may be useful in circumstances where access and manoeuvrability are restricted by the confines of the body cavity.

SUMMARY OF THE INVENTION

It is an object of this invention to provide an electrode assembly for improved removal of tissue immersed in an electrically conductive liquid.

According to a first aspect of this invention, an electrode assembly for the electrosurgical removal of tissue immersed in an electrically conductive liquid comprises an elongate support structure including at least a pair of conductors for carrying radio frequency electrosurgical currents, an electrically insulative body mounted at a distal end of the support structure and extending transversely with respect to the support structure, a transversely extending conductive tissue treatment electrode secured to one side of the insulative body and electrically connected to one of the conductors, and a transversely extending conductive return electrode secured to an opposite side of the insulative body. The ratio of the exposed surface area of the tissue treatment electrode to that of the return electrode is preferably relatively large, e.g. greater than 1:1. The applicants have found that optimum performance is achieved with the ratio in the range of from 1.25:1 to 2:1.

The insulative body preferably comprises a ceramic, generally cylindrical, element with the cylinder axis oriented transversely of the support structure, the tissue treatment electrode and return electrodes covering a downwardly directed and an upwardly directed surface respectively of the ceramic element, each being fixed to the element by means of an interlocking rib and groove arrangement which permits assembly without use of an adhesive. This allows the electrode assembly to operate at high temperatures, typically up to 500° C. or 600° C.

The tissue treatment or active electrode may be an arcuate plate secured directly to the downwardly directed surface of the ceramic element, and is preferably both thin and made of a relatively poor thermally conducting metal in order to hinder the transfer of heat from one part of the electrode to another. This is to assist formation and maintenance of a vapour pocket around the electrode. Surface irregularities in the form of ribs or alternatively shaped projections are provided to hinder thermal convection by flow of conductive liquid over the electrode and by trapping bubbles of vapour between them. In contrast, the return electrode is advantageously smooth, so as to achieve the converse effect, i.e. to discourage vaporisation of the conductive liquid on its surface. Placing the return electrode directly above the active electrode and on the opposite side of the insulator body, largely prevents it from contacting tissue but at the same time to be surrounded by the conductive liquid.

In the preferred electrode assembly, the shape and configuration of the electrode and insulative body are such that the minimum conduction path length between the tissue treatment electrode and the return electrode by conduction through the conductive liquid is greater than or equal to 1.5 mm. This may be achieved in a small assembly by forming the ceramic element so that it projects outwardly beyond the edges of the electrodes to provide a conduction path length which is greater than the geometric separation of the electrodes.

To provide for endoscope mounting, the support structure may comprise solely a pair of rigid wire-form conductors with a clip for attaching them to the telescope tube of the endoscope, and having distally branched arms which, at their distal ends, support the ceramic element and electrodes, one arm located on each respective lateral side of the element. Advantageously, grooves moulded in the upper and lower surfaces of the ceramic element receive inner ribs of the electrodes which are shaped to be locked positively in the grooves by having, for instance, a dovetail cross-section. The clip also serves to secure the conductor together so as to lie side-by-side proximally of the branch arms.

According to a second aspect of the invention, an electrode assembly for the electrosurgical removal of tissue immersed in an electrically conductive liquid comprises at least first and second electrodes mounted on an insulator, and at least a pair of conductor wires forming an elongate support structure for housing in an endoscope, the combination of the electrodes and the insulator being secured to distal ends of the wires with one wire of the pair connected to the first electrode and the other wire of the pair connected to the second electrode, and wherein the electrodes comprise transversely extending metallic coverings mounted on oppositely directed surfaces of the insulator.

BRIEF DESCRIPTION OF THE DRAWINGS

The invention will now be described by way of example with reference to the drawings in which:

FIG. 4 is a diagram showing the tip assembly in side elevation and the endoscopic field of view obtained with a 30° telescope:

FIG. 5 is a load characteristic graph illustrating the variation in load impedance produced by an electrode assembly such as that shown in FIGS. 1A to 1C and 2 to 4 when used close to a tissue surface in a conductive liquid, according to delivered output power;

DESCRIPTION OF THE PREFERRED EMBODIMENT

Figure 1:
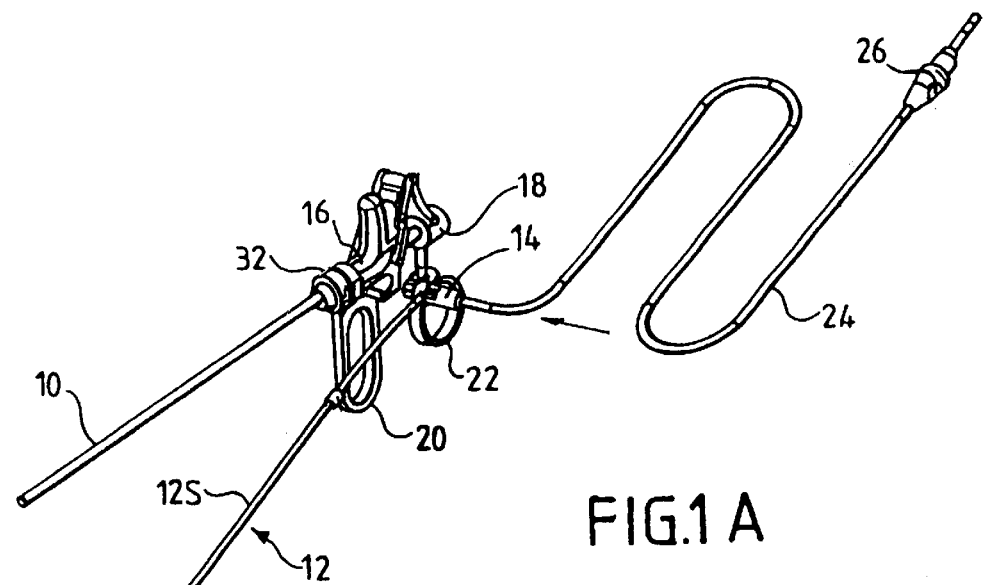
FIGS. 1A, 1B, and 1C are perspective views of an electrosurgical instrument comprising an endoscope and a reciprocal electrode assembly in accordance with the invention, the instrument being shown in three different stages of assembly.
Figure 1:
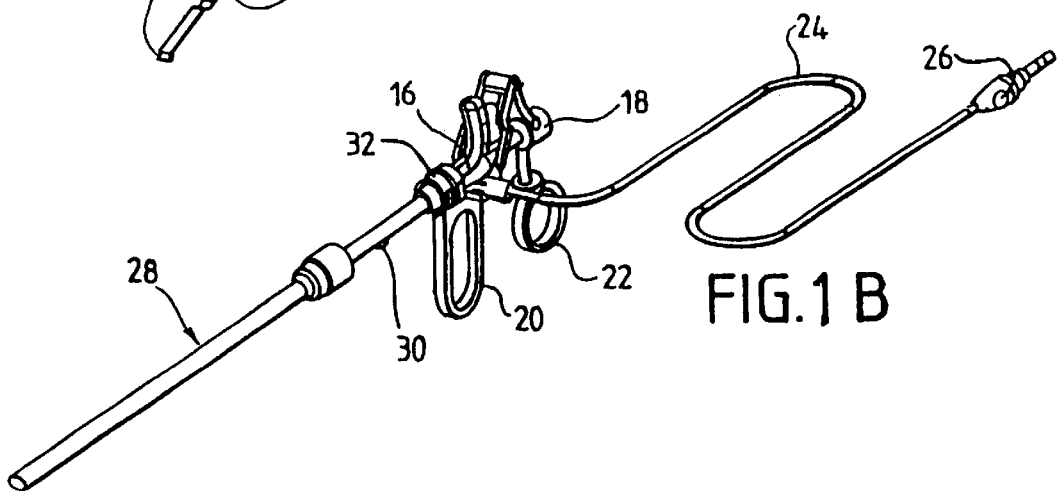
Figure 1:
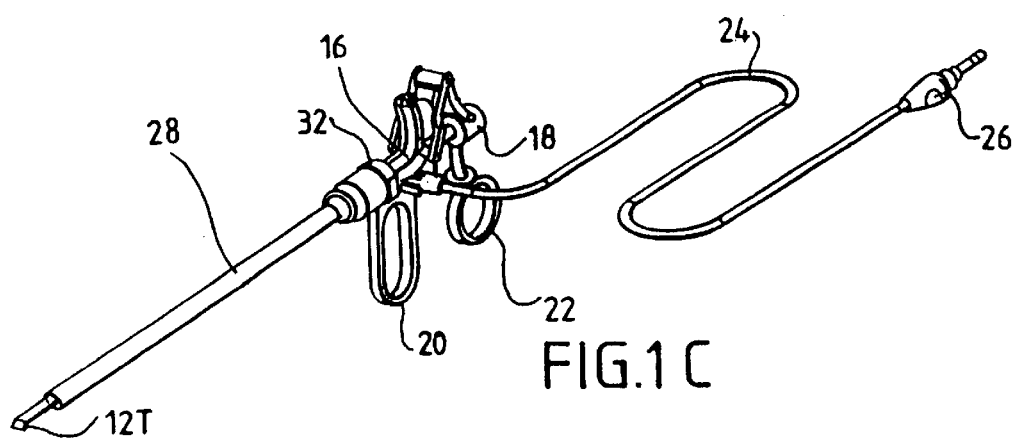

Referring to FIGS. 1A to 1C, an endoscopic electrosurgical instrument incorporating an electrode assembly in accordance with the invention includes a telescope 10 having an elongate hollow tube. The electrode assembly 12 has an elongate support structure 12S supporting a distal tip assembly 12T which includes a tissue treatment electrode and a return electrode. These elements will be described in more detail below with reference to the other figures. The support structure 12S takes the form of a pair of insulatively sleeved wire conductors which, towards their distal ends, carry a spring clip 12C for securing the electrode assembly to the tube of the telescope 10 in such a way that the electrode assembly may be reciprocated distally and proximally with the clip 12C sliding on the tube.

At their proximal ends, the support structure wires enter an insulative cable-mounting boss 14 which, when the instrument is assembled, is housed in a thermoplastics mounting block 16, as shown in FIGS. 1B and 1C. This mounting block 16 is slidable on the telescope 10 with respect to a collar assembly 18 secured to the telescope tube, relative movement between the electrode mounting block 16 and the collar assembly 18 being effected by squeezing together the two spring-loaded handles 20, 22 attached to each of them. As a result, the distal tip assembly 12T can be reciprocated relative to the end of the telescope 10. Inside the boss 14, connections are made between the conductor wires of the support structure 12S and a flexible cable 24 which is terminated in an in-line connector 26 for connecting the instrument to an electrosurgical radio frequency generator.

When the electrode assembly 12 has been secured to the telescope 10, an endoscope inner sheath 28 is passed over the combination of telescope and electrode assembly as shown in FIG. 1B and pushed home over a seal 30 and over the wire-form support structure to connect with a sealing block 32 associated with the insulation block 16, as shown in FIG. 1C. It will be noted that the distal end portion of the electrode assembly is now exposed beyond the distal end of the inner sheath 28.

A final stage of instrument assembly, not shown in the drawings, consists of fitting an outer sheath around the inner sheath 28, to mate with the sealing block 32, which has an aperture for directing conductive fluid from a fluid source (not shown) to the distal end of the instrument.

Figure 2:
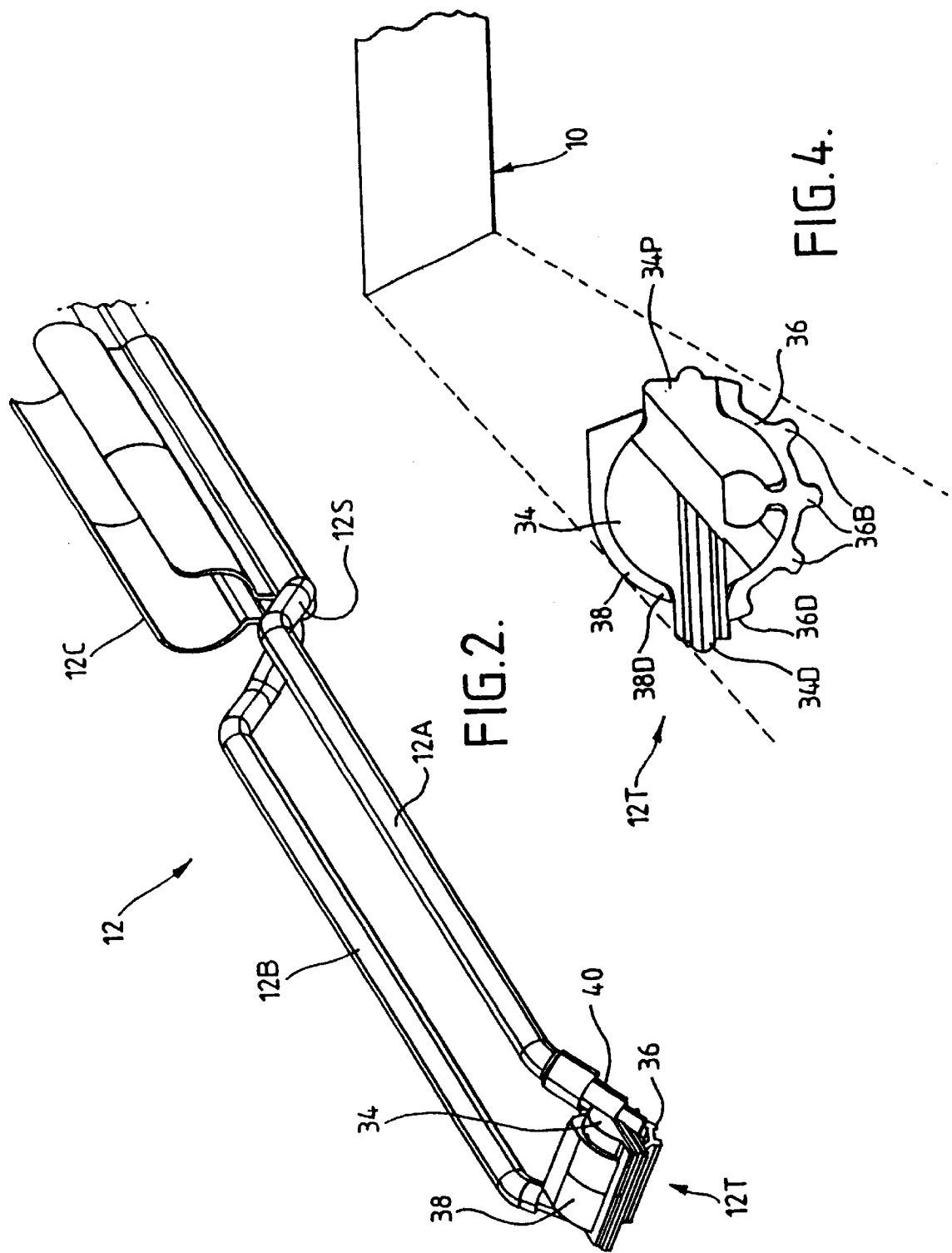
FIG. 2 is an enlarged perspective view of a distal portion of the electrode assembly forming part of the instrument shown in FIGS. 1A to 1C.

As shown in FIG. 2, the distal end portion of the support structure 12S beyond the telescope clip 12C is characterised by the branching of the pair of conductors into two laterally spaced conductor arms 12A, 12B. As will be seen from the drawing, the arms 12A, 12B are kinked at the branching point so as to lie on opposite sides of the telescope distally of the branching point and just distally of the end of the telescope 10 they are bent downwardly below the end of the telescope to support the distal tip assembly 12T at a position below the axis of the telescope 10. Except for their extreme distal end portions, the conductors forming the support structure are sleeved with a heat shrink material throughout their length.

The distal tip assembly 12T is a bipolar instrument working tip with a comparatively large area tissue treatment electrode designed for removing large volumes of tissue by tissue vaporisation. An example of such tissue is that associated with a condition known as benign prostatic hypertrophy (BPH). BPH produces an enlargement of the prostate which restricts the flow of urine from the bladder through the urethra, which it surrounds. The procedure entails the removal of all the tissue within a walnut-shaped capsule, which restores normal urine flow. A typical weight of tissue removed is 30 to 40 grams.

Figure 3:
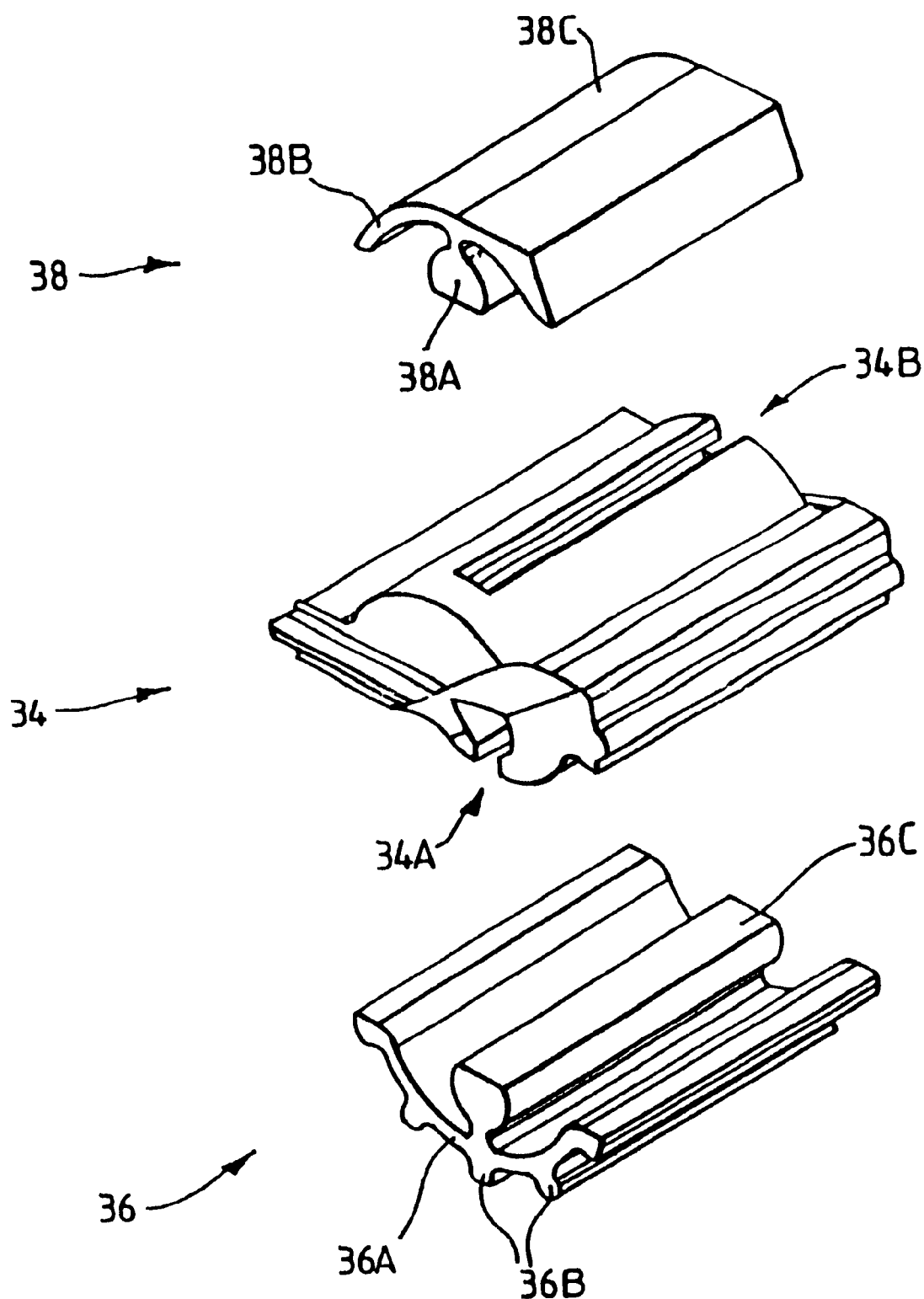
FIG. 3 is an exploded perspective view of an instrument tip assembly.

Referring to FIG. 2 and FIG. 3 together, the distal tip assembly 12T comprises a ceramic insulator body 34 of generally cylindrical configuration, extending transversely between the extreme distal end portions of the conductor arms 12A, 12B, a thin part-cylindrical stainless steel tissue treatment or active electrode 36 which covers a lower surface portion of the insulator body 34, and a stainless steel return electrode 38 covering an upwardly directed surface of the insulator body 34, i.e. on the opposite side of the insulator body 34 from the active electrode 36. The return electrode 38 is, therefore, directly above the active electrode 36 and at substantially the same position in the longitudinal direction of the electrode assembly 12. Both electrodes 36, 38 extend transversely between the extreme distal ends of the conductor arms 12A, 12B and each is secured directly to the ceramic insulator without the use of adhesive. There is no air gap between electrodes 36, 38 and insulator body 34.

As is shown clearly in FIG. 3, the active electrode 36 has, in addition to its part-cylindrical base lamina 36A, a plurality of transversely extending parallel outwardly projecting integral ribs 36B. These serve to lower the power threshold of the vaporisation of the electrode assembly by hindering heat convection away from the electrode and by trapping small pockets of saline vapour, particularly when the active electrode is placed near the surface of the tissue to be treated. The function of the ribs 36B is enhanced by arranging for the electrode exposed surface to be microscopically roughened. This roughening can be engineered or designed to occur during use as a result of the spark erosion which occurs on the exposed surface.

The active electrode 36 is constructed of stainless steel which has relatively poor thermal conductivity. This, in conjunction with the low thermal mass yielded by the small thickness of the base lamina 36A (the thickness being in the region of from 0.15 mm to 0.5 mm, hinders the transfer of heat from one portion of the active electrode to another, so that should a portion of the electrode 36 be wetted by the conductive liquid, heat is not quickly dissipated to the wetted portion from other portions of the electrode. Supporting the tip assembly 12T on wires also reduces heat dissipation to the remainder of the electrode assembly. These measures all help to promote vaporisation of the conductive liquid over the surface of the active electrode 36.

As will be seen also from FIG. 3, the active electrode 36 has an integral undercut inner rib 36C running parallel to the transverse ribs 36B. This allows the active electrode 36 to interlock positively in a complementary undercut groove 34A in the ceramic insulator body 34. Groove 34A extends transversely of the insulator body 34, and is open at one lateral end of the insulator body 34 but closed at the other. Consequently, the active electrode 36 may be mounted to the insulator body by sliding inner rib 36C transversely into the open end of groove 34A until it is pushed completely home with the rib 36C abutting the closed end.

A similar undercut groove 34B is cut into the upper surface of the insulator body 34 to receive a corresponding inner rib 38A of the return electrode 38, also shown in FIG. 3. In this case, however, the upper groove 34B opens to the opposite lateral end of the insulator body from the open end of the lower groove 34A. Like the lower groove 34A, it is closed at its other end. As a result, the return electrode 38 can be mounted to the insulator body 34 in the same manner as the active electrode, by sliding from one side, but in this case from the other side.

Adjacent the open ends of their respective grooves 34A, 34B, each electrode 36, 38 is welded to a respective one of the conductor arms 12A, 12B. Proximally, the arms 12A, 12B are fastened together. This, together with the resilience of the arms 12A, 12B and a spring bias towards each other, acts to retain each electrode 36, 38 against the closed end of its respective groove 34A, 34B, whereby the distal tip assembly remains assembled without the use of adhesive material.

The return electrode has no outer ribs, but acts as an oppositely directed generally part-cylindrical shell portion 38B with a smooth outer surface 38C. In practice, the return electrode 38, like the active electrode 36, is made of a stainless steel. However, it can be made of a material of higher thermal conductivity to supplement the effect of the smooth surface 38C in hindering vaporisation at the return electrode 38.

The insulator body 34 separates the electrodes 36, 38 in such a way that conduction through the tissue to be treated as the path of least electrical resistance and so that direct arcing between active and return electrodes is largely prevented. The applicants have found that the minimum conductive path length between the electrodes for achieving this in most circumstances is 1.5 mm. The manner in which this clearance is obtained is best seen in the diagrammatic side elevation of FIG. 4. In this embodiment of the electrode assembly, the insulator body 34 is shaped to reduce as far as possible the degree to which it and electrodes 36, 38 block the surgeon's view of the tissue being treated when using the telescope 10. The optical properties of the preferred telescope 10 are such that its viewing angle is centred on a viewing axis lying at 25° to 30° to the axis of the telescope tube, directed towards the distal tip assembly and the surrounding tissue.

The insulator body 34 is shaped and mounted so as to define a separation plane between the electrodes 36, 38 which plane lies substantially parallel to the support structure 12S (see FIGS. 1A and 2), and with the distal edges of the electrodes 36, 38 closer together than their proximal edges. To achieve a conductive path length of at least 1.5 mm between pairs of edges (i.e. between the distal edges and the proximal edges respectively), the insulator body 34 has a distal rib 34D which projects well beyond the distal edges 36D, 38D of the electrodes. Consequently, the conductive path length between these distal electrode edges is considerably greater than their geometric separation. On the proximal side, the insulator body 34 has a proximal separating rib 34P which is wider than the distal rib 34D and projects beyond the main cylindrical mass of body 34 to a relatively small degree. In this way, as can be seen from the dotted lines in FIG. 4, the overall size of the distal tip assembly in the field of view of telescope 10 is reduced whilst maintaining the ability to remove tissue at different angles of attack, due to the semicircular crosssection of the active electrode 36. At the same time, the short projecting rib 34P on the proximal side has the benefit of making the active electrode 36 visible so that the surgeon can see when a vapour pocket is formed.

In order to keep the size of the distal tip assembly small despite its relatively large electrode areas, the wire-form conductor arm 12A is located close to the return electrode. An additional ceramic sleeve 40 around the distal end portion of the arm 12A acts as a high temperature insulator between the two.

The proximal-distal circumferential extent and the width of the active electrode are respectively about 1.8 mm and 4 mm, giving a geometrical area of the lamina of about 7 mm$^2$. In the general sense a part-cylindrical or outer area greater than 5 mm is preferred. The actual exposed surface area of the active electrode when mounted on the electrode is typically in the region of 15 mm$^2$ upwards, due to the surface projections and lateral edge surfaces. This Figure is preferably in the range of from 15 to 35 mm$^2$ but can be as high as 50 or 60 mm$^2$.

It will be understood that the larger the area of the active electrode, the greater is the rate at which tissue can be removed, providing sufficient power can be dissipated at the electrode and a vapour layer maintained over its entire exposed surface.

With the above requirements in mind, the electrical behaviour of the electrode assembly when the active and return electrodes 36, 38 are immersed in the conductive liquid will now be considered with reference to the graph of FIG. 5. This illustrates the hysteresis which exists between tissue desiccation and tissue vaporising modes of the assembly when it is adjacent the surface of the tissue to be treated. Removal of tissue, achieved by vaporisation of the tissue, occurs when the active electrode is covered with a layer of vapour. Without such a vapour layer, the tissue is merely desiccated. When the electrode assembly is immersed in a conductive liquid without any radio frequency power applied, there is an initial impedance "r" at point "O", the magnitude of which is defined by the geometry of the electrode assembly and the electrical conductivity of the liquid. The higher the value of "r", the greater is the propensity of the electrode assembly to enter the vaporisation mode. When RF power is applied to the assembly, the liquid is heated. In the case of normal saline (0.9%w/v), the temperature coefficient of the liquid is positive, so that the corresponding impedance coefficient is negative. Thus, as power is applied, the impedance initially falls and continues to fall with increasing power dissipation to point "B" (see FIG. 5), at which point the saline in intimate contact with the electrode assembly reaches boiling point. Small vapour bubbles form on the surface of the active electrode 36, and the impedance then starts to rise. After point "B", as power is increased further, the positive power coefficient of impedance is dominant, so that small increases in power now bring about large increases in impedance.

As a vapour layer forms from the vapour bubbles, there is an increase in the power density at the remaining electrode/saline interface. There is, however, an exposed area of the active electrode not covered by vapour bubbles, and this further stresses the interface, producing more vapour bubbles and thus even higher power density. This is a run-away condition, with an equilibrium point only occurring once the electrode is completely enveloped in vapour. It is possible to avoid the run-away condition by limiting applied voltage thereby preventing power dissipation into higher impedance loads. For a given set of variables, there is a power threshold before this new equilibrium can be reached (point "C").

The transition from point "C" to a vaporise equilibrium state follows the power/impedance curve for the RF stage of the generator coupled to the instrument. The nature of this curve affects the stability of the vaporisation equilibrium state, and is described in more detail below. Once in this vaporisation equilibrium state, the impedance rapidly increases to around 1000 ohms, the absolute value depending on system variables. The vapour layer is then sustained by discharges across the layer between the active electrode and the vapour/saline interface or the vapour/tissue interface depending on the proximity of the tissue surface. The majority of power dissipation occurs within the vapour layer, with consequent heating of the active electrode. The amount of energy dissipation and the size of the vapour pocket depends, on the output voltage. If this is too low, the pocket will not be sustained, and if it is too high, the electrode assembly will be destroyed. It should be noted that, if power were delivered at the same level as point "C", the resulting voltages would cause electrode destruction. The normal operating point for an electrode used for vaporisation is illustrated as point "D". This point is defined uniquely by the combination of the impedance power characteristic for the electrode assembly, in conjunction with the vaporise voltage limit which appears as curve $V_v$ in FIG. 5.

The dotted line E indicates the power level above which electrode destruction occurs. As the power is reduced, the impedance falls until, at point "A" the vapour pocket collapses and the electrode assembly reverts to the desiccation mode. At this point, power dissipation within the vapour pocket is insufficient to sustain it, so that direct contact between the active electrode and the saline or the tissue is re-established, and the impedance falls rapidly. The power density at the active electrode also falls, so that the temperature of the saline falls below boiling point. The electrode assembly is then in a stable desiccation mode, below the desiccation voltage limit indicated by curve $V_D$.

To operate the electrode assembly in vaporisation mode, power is applied to maintain an operation point on the curve between "D" and point "A". The upper part of this curve has been found to be most suitable for tissue removal by vaporisation. As stated above, the load impedance presented to the generator in this region of the graph is about 1000 ohms. The vaporisation voltage limit (curve $V_v$) is set in the range of from 250 V to 600 V peak. 300 V peak is a typical value.

Figure 6:
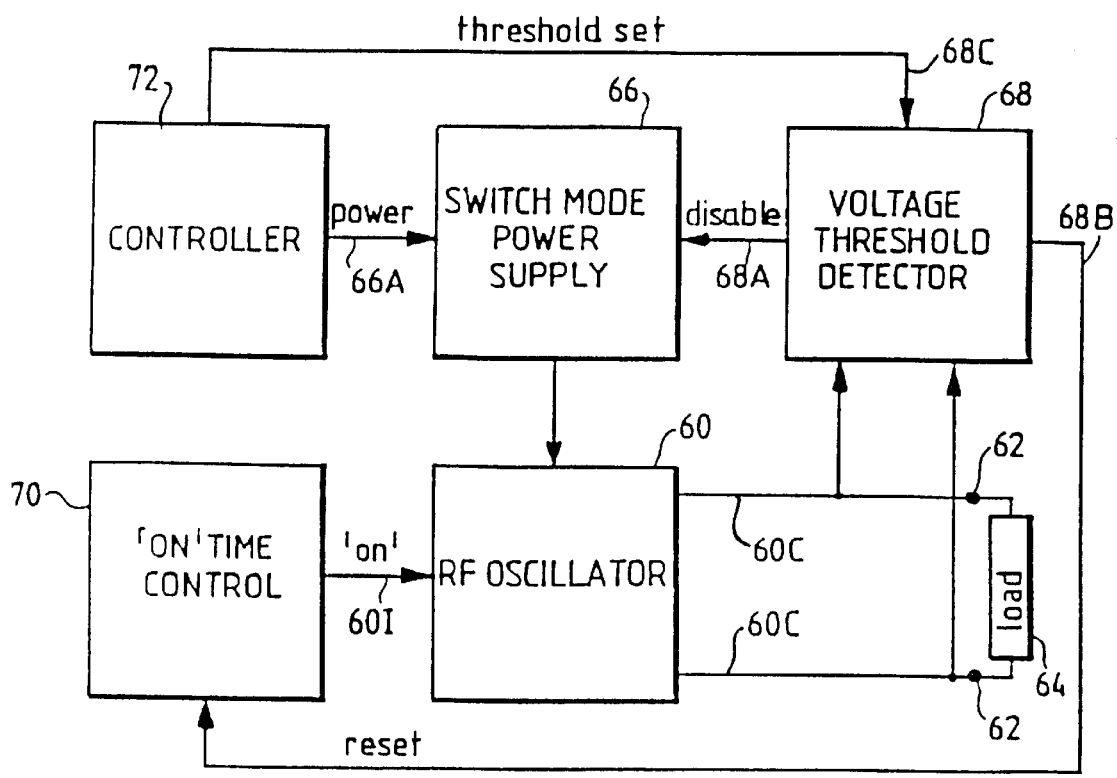
FIG. 6 is a block diagram of an electrosurgical generator suitable for connection to the instrument of FIGS. 1A to 1C.

A generator suitable for driving the electrode assembly so as to meet the requirements set out above is illustrated in block diagram form in FIG. 6.

Referring to FIG. 6. the generator comprises a radio frequency (RF) power oscillator 60 having a pair of output connections 60C for coupling via output terminals 62 to the load impedance 64 represented by the electrode assembly when in use. Power is supplied to the oscillator 60 by a switched mode power supply 66.

In the preferred embodiment, the RF oscillator 60 operates at about 400 kHz, with any frequency from 300 kHz upwards into the HF range being feasible. The switched mode power supply typically operates at a frequency in the range of from 25 to 50 kHz. Coupled across the output connections 60C is a voltage threshold detector 68 having a first output 68A coupled to the switched mode power supply 16 and a second output 68B coupled to an "on" time control circuit 70. A microprocessor controller 72 coupled to the operator controls and display (not shown) is connected to a control input 66A of the power supply 66 for adjusting the generator output power by supply voltage variation and to a threshold-set input 68C of the voltage threshold detector 68 for setting peak RF output voltage limits.

In operation, the microprocessor controller 72 causes power to be applied to the switched mode power supply 66 when electrosurgical power is demanded by the surgeon operating an activation switch arrangement which may be provided on a handpiece or footswitch. A constant or alternating output voltage threshold is set via input 68C according to control settings on the front panel of the generator (see FIG. 1). Typically, for desiccation or coagulation the threshold is set at a desiccation threshold value between 150 volts and 200 volts. When a vaporisation output is required as with the electrode assembly described above, the threshold is set to a value in the range of from 250 or 300 volts to 600 volts. These voltage values are peak values. Their being peak values means that for desiccation at least it is preferable to have an output RF waveform of low crest factor to give maximum power before the voltage is clamped at the values given. Typically a crest factor of 1.5 or less is achieved.

When a blended output is required, the voltage threshold set via input 68C is constantly alternated between the value for desiccation or coagulation and the value for cutting or vaporisation.

When the generator is first activated, the status of the control input 601 of the RF oscillator 60 (which is connected to the "on" time control circuit 70) is "on", such that the power switching device which forms the oscillating element of the oscillator 60 is switched on for a maximum conduction period during each oscillation cycle. The power delivered to the load 64 depends partly on the supply voltage applied to the RF oscillator 60 from the switched mode power supply 66 and partly on the load impedance 64. If the supply voltage is sufficiently high, the temperature of the liquid surrounding the electrodes of the electrode assembly may rise to such an extent that the liquid vaporises, leading to a rapid increase in load impedance and a consequent rapid increase in the applied output voltage across terminals 12.

As described above with reference to FIG. 5, different voltage thresholds are set. depending on whether the generator is to be used in a desiccate mode or a vaporise mode. In both cases, trigger signals are sent to the "on" time control circuit 70 and to switched mode power supply 66 when the respective selected voltage threshold is reached. The "on" time control circuit 70 has the effect of virtually instantaneously reducing the "on" time of the RF oscillator switching device. Simultaneously, the switched mode power supply is disabled so that the voltage supplied to oscillator 60 begins to fall.

Figure 7:
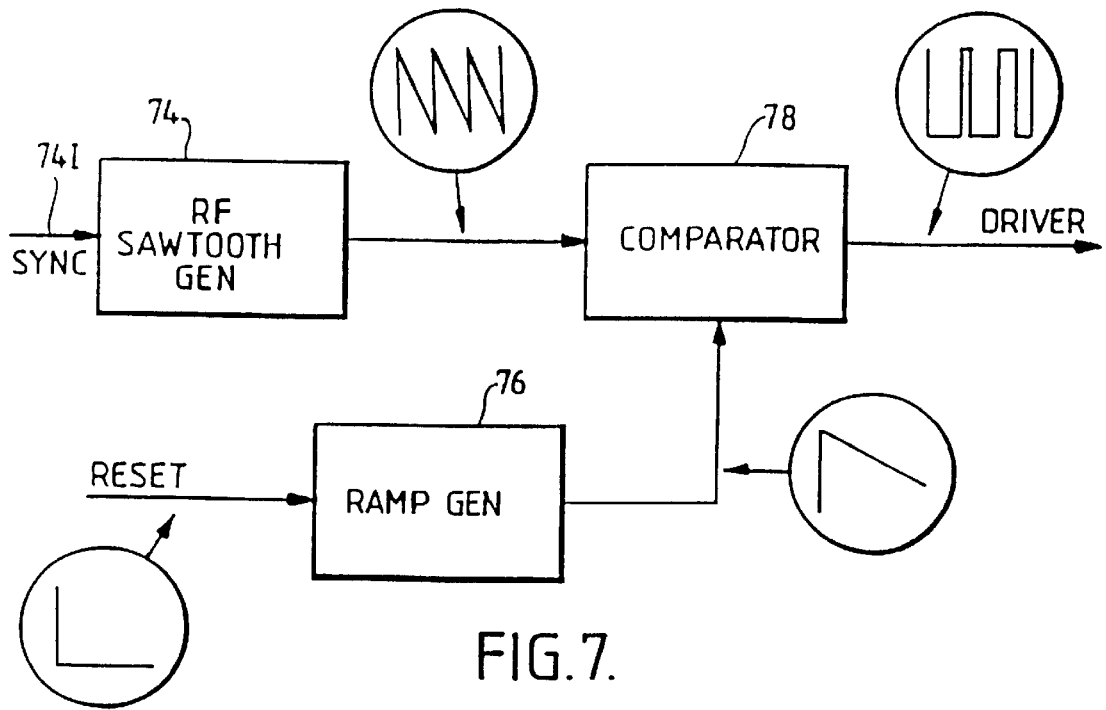
FIG. 7 is a block diagram of part of the control circuitry of the generator of FIG. 6.

Subsequent control of the "on" time of individual cycles of the oscillator 60 will be understood by considering the internal configuration of the "on" time control circuit 20 which is shown in FIG. 7. The circuit comprises an RF sawtooth generator 74 (synchronised at the RF oscillation frequency by a synchronisation signal derived from the oscillator and applied to a synchronisation input 741), and a ramp generator 76 which is reset by a reset pulse from the output 68B of the voltage threshold detector 68 (see FIG. 6) produced when the set threshold voltage is reached. This reset pulse is the trigger signal referred to above. The "on" time control circuit 70 further comprises a comparator 78 for comparing the sawtooth and ramp voltages produced by the sawtooth and ramp generators 74 and 76 to yield a square wave control signal for application to the input 601 of the RF oscillator 60. As shown by the waveform diagrams in FIG. 7, the nature of the sawtooth and ramp waveforms is such that the mark-to-space ratio of the square wave signal applied to the oscillator 60 progressively increases after each reset pulse. As a result, after a virtually instantaneous reduction in "on" time on detection of the output voltage reaching the set voltage threshold, the "on" time of the RF oscillator is progressively increased back to the original maximum value. This cycle is repeated until the supply voltage for the oscillator from power supply 66 (FIG. 6) has reduced to a level at which the oscillator can operate with the maximum conduction period without the output voltage breaching the set voltage threshold as sensed by the detector 68.

The output voltage of the generator is important to the mode of operation. In fact, the output modes are defined purely by output voltage, specifically the peak output voltage. The absolute measure of output voltage is only necessary for multiple term control.

However, a simple term control (i.e. using one control variable) can be used in this generator in order to confine the output voltage to predetermined limit voltages. Thus the voltage threshold detector 68 shown in FIG. 6 compares the RF peak output voltage with a preset DC threshold level, and has a sufficiently fast response time to produce a reset pulse for the "on" time control circuit 70 within one RF half cycle.

In the generator described above with reference to FIGS. 6 and 7, power reduction in response to voltage threshold detection takes place in two ways (a) an instantaneous reduction in RF energy supplied to the resonant output circuit of the oscillator, and (b) a shut down of DC power to the oscillator for one or more complete cycles of the switched mode power supply (i.e. typically for a minimum period of 20 to 40 $\mu$s).

In the preferred embodiment, the instantaneous power reduction is by at least three quarters of available power (or at least half voltage) from the DC power supply, but continuous voltage threshold feedback continually causes a reduction in delivered power from the DC power supply. Thus, a high speed response is obtained in the RF stage itself, with the DC supply voltage tracking the reduction to enable the RF stage to return to a full duty cycle or mark-to-space ratio, thereby enabling further rapid power reductions when the voltage threshold is again breached.

The rapid response on reaching the peak vaporise threshold voltage Vv effectively prevents runaway destruction of the electrode along portion "E" of the impedance power curve shown in FIG. 5. Effective control of the vaporisation mode is also aided by the fact that the preferred generator has an output impedance set to about 160 ohms. The effect of this choice will be evident from the following description with reference to FIGS. 8 and 9 which are graphs showing the variation of the output power which can be produced by the generator into different load impedances.

Figure 8:
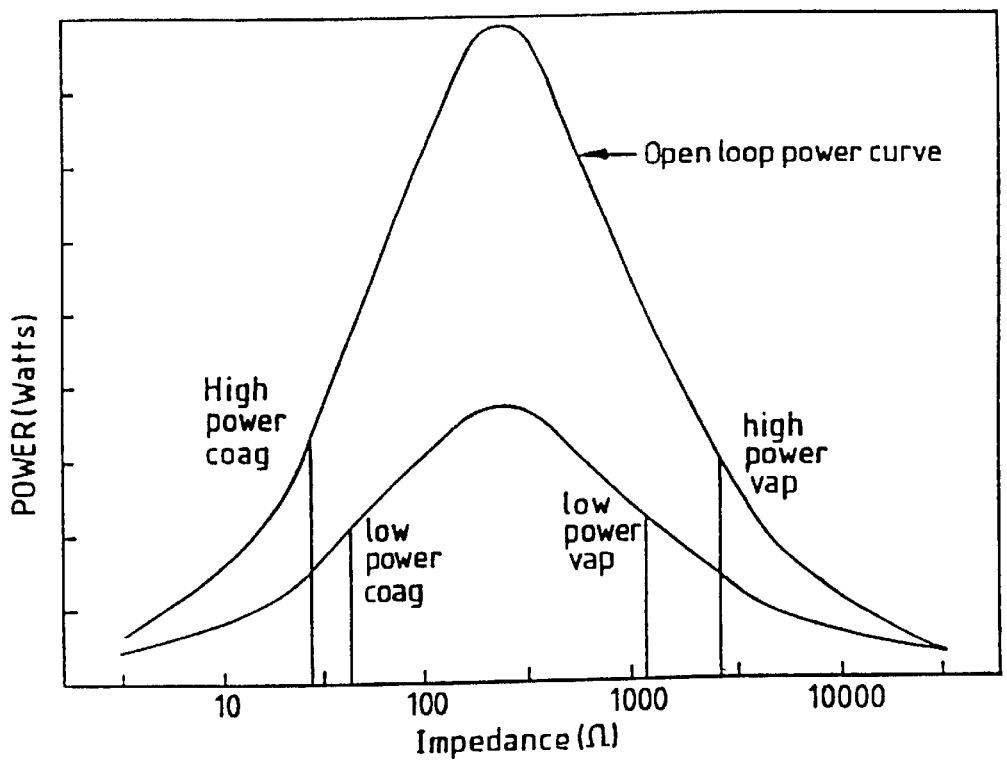
FIG. 8 is a graph showing the variation of output power produced by the generator as a function of the load impedance presented to it by the electrode assembly, the output power variation being shown in two operation modes of the generator.

Referring to FIG. 8, the power delivered to the load is here shown as a function of load impedance for two different oscillator supply voltage settings. In both cases, it will be seen that, to the left of the power/impedance peak, an increase in load impedance leads to an increase in output power and, hence, an increase in output voltage. At higher impedances, to the right of the peaks, the voltage continues to increase, albeit less aggressively, as impedance increases.

One of the features of the preferred generator is that the output stage operates as an open loop oscillator with an output impedance (corresponding to the peaks in FIG. 8) of about 160 ohms. This is considerably lower than the output impedance of conventional generators used for underwater electrosurgery, and contributes to the ability to prevent runaway arcing behaviour and consequent excessive tissue damage and electrode burn-out.

It should be understood that when the generator is used for desiccation, steam envelope generation at the electrode and arcing should be prevented. Conversely, for cutting or vaporisation, steam envelope generation and arcing are required, but to a level consistent with achieving the required tissue effect and the avoidance of electrode burn-out. Operating points for low and high power desiccation and cutting or vaporisation are shown in FIG. 8.

In order to traverse from a desiccation mode to the vaporisation mode, a high power burst is required, hence the positioning of the power/load curve peak between the desiccation and cut or vaporisation operation points on the curve. By allowing the output power to increase with impedance in this way, a high power burst of sufficient energy to create arcing is achieved despite the initial low impedance presented by the electrodes. As the supply voltage to the oscillator is increased, the electrode assembly has a greater propensity to flip into the cut mode, whilst at lower supply voltage levels, the bistable nature of the output, although more pronounced, tends towards the desiccation state. The bistable properties arise not only from the electrode impedance behaviour, but also from the shape of the power/load impedance curve. The flatter the load curve, the more constant the output power across a band of impedances and the less pronounced the effect.

Referring to FIG. 8, it will be appreciated that in the cut or tissue vaporisation mode, a power equilibrium point is achieved by virtue of the decreasing output power as impedance increases.

The applicants have found that the inherent equilibrium described above may be insufficient to maintain a stable vaporisation state. It is for this reason that the RF output voltage from the RF oscillator 60 (FIG. 6) is limited, the limiting occurring extremely rapidly, typically with a response time of 20 $\mu$s or less. Excessive radio frequency interference is avoided by linear variation of the oscillator switching device "on" time in response to a feedback signal from the voltage threshold detector. This technique is used in conjunction with the RF oscillator having a comparatively low output Q when matched to the load, this Q being sufficient to suppress switching noise without inordinately damping the response to output voltage threshold detection.

Figure 9:
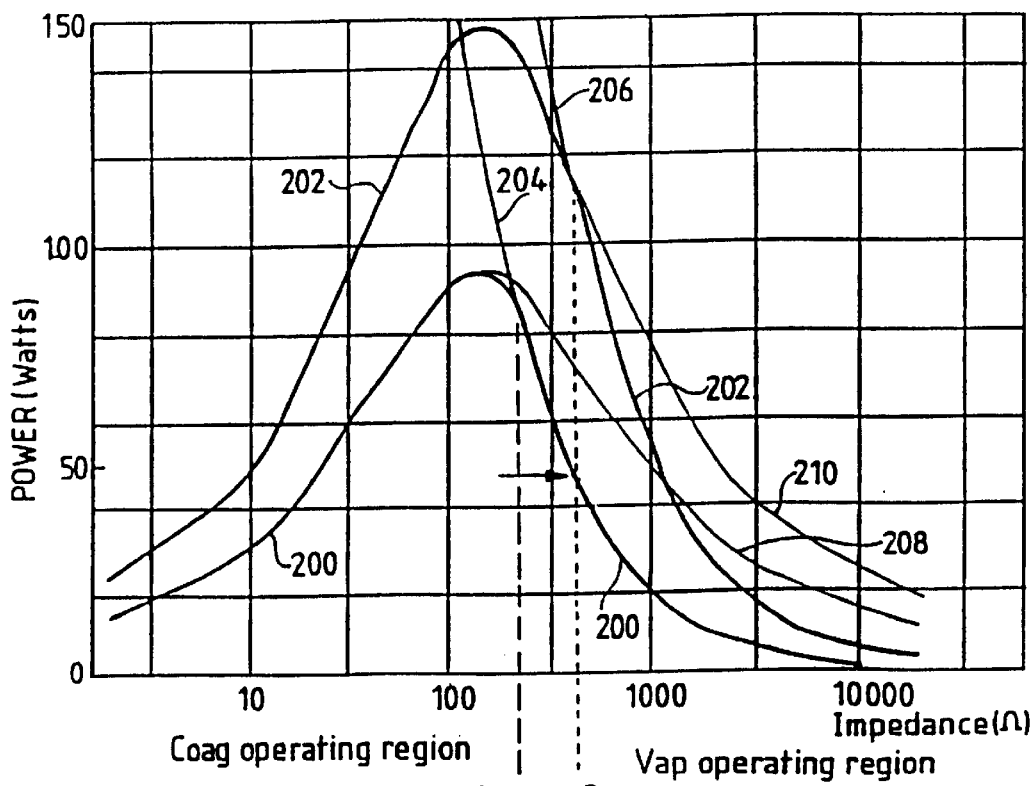
FIG. 9 is a graph showing the variation of output power for the generator as a function of load impedance after modification of the generator characteristics in response to output voltage sensing.

By way of example, the effect of voltage threshold control for a particular electrode configuration is shown in FIG. 9. The heavy lines 200, 202 indicate the modified power/load impedance characteristics. For desiccation, shown by line 200, the switched mode power supply is set to produce a peak (matched) open loop output power of between 75 watts and 110 watts, with the actual peak power in this case being about 90 watts. For cutting and vaporisation (shown by line 202), the continuous peak power can be between 120 watts and 175 watts. In this case it is 150 watts. As examples, the voltage thresholds are set at 180 volts peak for desiccation and 300 volts peak for cutting, as illustrated by the hyperbolic constant voltage lines 204 and 206 respectively. The power/impedance curves follow the respective constant voltage threshold lines to the right of their intersection with the unmodified open loop curves 208 and 210. Thus, it will be understood that the desiccation threshold line represents the maximum voltage that can be achieved in the desiccation mode before arcing is produced, whilst the cut or vaporisation threshold line limits the cutting or tissue vaporisation performance to achieve the desired tissue effect and, in the extreme, to avoid electrode burn-out. The desiccation threshold line also represents a voltage insufficient to achieve arcing for cutting or vaporising tissue.

A significant feature of the generator characteristic for electrosurgical cutting or tissue vaporisation is that at peak power (matched impedance) the load impedance lies between the impedances corresponding to the threshold voltages at that power level. In contrast, in the desiccation mode, the power/load impedance characteristic has a power peak at an impedance lying below the desiccation threshold line at that power level.

In practice, the output power in the desiccation mode will be higher than in the cutting or tissue vaporisation mode. The reason for this statement (despite the apparent contradiction with the load curves in FIG. 9) is that the equilibrium points described above lie at different points on the respective curves. To ensure tissue vaporisation, the high peak power of the higher curve is required to reach the cut or vaporisation threshold line (corresponding to 300 volts peak). The vaporisation mode then follows the cutting or vaporisation threshold line. The operating point is defined by the load impedance created when a suitable level of arcing is occurring. Typically, the load impedance in these circumstances is greater than 1000 ohms. The generator is configured to give boosted power for an initial period between 100 ms and 1 second at a level typically about 25% higher than the continuous vaporisation power output setting. Thus, in the present embodiment, output power is boosted to about 200 W for 400 ms from the moment of actuation of the footswitch for activating the application of RF power to the electrode assembly. This largely ensures vaporisation of the conductive liquid over the active electrode, even when it is clean and no spark erosion has occurred. After this boost period, although a full 150 watt peak power is available to ensure that vapour pockets are maintained to promote arcing for vaporisation, the actual power drawn during tissue vaporisation for this particular electrode assembly described above may be between 50 watts and 100 watts. This situation is more easily understood if reference is also made to FIG. 5. The activation of the initial boosted output is effected by arranging for a boost signal to be applied to the switched mode power supply 66 by the controller 72 via line 66A for the said initial period (see FIG. 6). The power threshold of vaporisation decreases once spark erosion has roughened the exposed surface.

The generator is described in more detail in the above-mentioned European Patent Application No. 0754437.

It will be appreciated from the above description of the electrode assembly that both the return and the active electrodes have the potential to form a vapour pocket. In conventional bipolar electrodes, vaporisation of the liquid is confined largely to the active electrode by providing higher energy densities at the active electrode than at the return electrode, by arranging for the exposed surface area of the active electrode to be substantially smaller than that of the return electrode. In contrast, the electrode assembly described above with reference to FIGS. 1A to 1C and to 2 to 4 typically has an active to return electrode surface area ratio exceeding 1:1 and more typically is in the range of from 1.25:1 to 2:1 (active:return). Here, the surface area is that area which is in contact with the conductive liquid when completely immersed, before activation by the electrosurgical generator. The present electrode assembly has been designed such that the configuration of the return electrode discourages vapour pocket entrapment and formation on its surface, whilst such entrapment is provided by the features of the active electrode so that, once vapour bubbles begin to form, they are trapped in the cavities between the ribs and in the microscopic indentations provided by the surface roughness, so as then to reduce the effective contact area of the electrode with the conductive liquid. This promotes rapid formation of a vapour pocket completely covering the active electrode. Placing the active electrode adjacent the tissue surface reduces the cooling effect of convection currents in the liquid, allowing the trapped saline to absorb the electrosurgical power and to rapidly reach and maintain the boiling point of the liquid. Once boiling has commenced, the grooves between the ribs slow down the migration of the emerging vapour bubbles away from the active electrode surface so as to encourage them to coalesce into a vapour pocket. The return electrode, being located directly above the active tip is positioned to avoid contact with tissue, therefore ensuring that it is constantly surrounded by conductive liquid which cools its surface, thereby dissipating energy throughout a large volume of liquid.

Once a vapour pocket has formed, the ribs of the active electrode promote arc propagation because they form natural areas of high ion concentration. The ribs are rounded to avoid accidentally tearing the tissue to be treated. The ribs are oriented at 90° to the direction of travel of the electrode over the tissue surface. It has been found that this arrangement causes the best axial retention of vapour, while the sides of the vaporised trench in the tissue limit the amount lost from the lateral sides of the electrode assembly. A secondary benefit of retaining the vapour in this way is that the migration of bubbles away from the tip is reduced, thereby improving the surgeon's view of the operative site. This orientation of the active electrode also produces the most even tissue removal across the width of the assembly.

To further facilitate even tissue removal, as the electrode is moved over the tissue, it is swung through an arc, intended to match the curvature of the tissue to be removed. For this reason, the active tip has its semicircular cross-section to provide the maximum surface area for tissue removal at all stages of both the forward and the return stroke.

The above-described electrode assembly is intended particularly for electro-vaporisation of the prostate gland (EVAP) and other variants of the procedure commonly referred to as transurethral resection of the prostate (TURP), typically by interstitial ablation of the prostate gland by a perurethral route, whether performed for benign or malignant disease; transurethral removal of urinary tract tumours as they may arise as primary or secondary neoplasms, and further as they may arise anywhere in the urological tract from the calyces of the kidney to the external urethral meatus.

It is evident from the scope of the applications of the invention that it has further additional applications for vaporisation of tissue in general laparoscopic, endoscopic gastroenterological surgery, hysteroscopic, thoracoscopic, and neurosurgical procedures, being particularly useful in the removal of diseased tissue and neoplastic disease whether benign or malignant.

The surgical site is generally bathed in a continuous flow of conductive liquid such as saline solution either to fill and distend an anatomical body cavity or space such as the human uterus or one created surgically. In addition, a locally irrigated environment may be created around the tip of the electrode assembly in a gas-filled cavity. The irrigating fluid may be aspirated from the surgical site to remove products created by the application of RF energy, together with tissue, debris or blood.

What is claimed is:

1. An electrode assembly for the electrosurgical removal of tissue immersed in an electrically conductive liquid, wherein the assembly comprises an elongate support structure including at least a pair of conductors for carrying radio frequency electrosurgical currents, an electrically insulative body mounted at a distal end of the support structure and extending transversely with respect to the support structure, a transversely extending conductive tissue treatment electrode secured to a lower side of the insulative body and electrically connected and fixedly secured to a first one of the conductors, and a transversely extending conductive return electrode secured to an opposite and upper side of the insulative body and electrically connected and fixedly secured to a second one of the conductors.

2. An electrode assembly according to claim 1, wherein the ratio of the exposed surface area of the tissue treatment electrode to that of the return electrode is greater than 1:1.

3. An electrode assembly according to claim 2, wherein the said ratio is in the range of from 1.25:1 to 2:1.

4. An electrode assembly according to claim 1, wherein the tissue treatment electrode is a metallic lamina lying on an outer surface of the insulative body.

5. An electrode assembly according to claim 4, wherein the lamina, excluding any surface projections, has a thickness in the range of from 0.15 mm to 0.5 mm.

6. An electrode assembly according to claim 4, wherein the lamina has a thermal conductivity of less than 2 $WK^{-1}$.

7. An electrode assembly according to claim 6, wherein the lamina is formed of stainless steel.

8. An electrode assembly according to claim 1, wherein the tissue treatment electrode has a plurality of surface projections.

9. An electrode assembly according to claim 8, wherein the surface projections comprise transversely extending ribs.

10. An electrode assembly according to claim 8, wherein the return electrode is generally smooth-surfaced.

11. An electrode assembly according to claim 1, wherein the insulative body is formed from a ceramic material.

12. An electrode assembly according to claim 11, wherein at least the tissue treatment electrode is generally in the form of a plate, and the plate and the insulative body have complementary shape features providing interlocked mounting of the plate on the body.

13. An electrode assembly according to claim 1, wherein the combination of the insulative body, the tissue treatment electrode and the return electrode forms a generally cylindrical member having an axis extending transversely of the support structure, the said electrodes forming conductive, generally part-cylindrical shell elements separated from each other along transversely extending proximal and distal exposed parts of the insulative body.

14. An electrode assembly according to claim 13, wherein the shape and configuration of the electrodes and the insulative body are such that the minimum conduction path length between the tissue treatment and return electrodes when they are immersed in a conductive liquid is greater than or equal to 1.5 mm.

15. An electrode assembly according to claim 14, wherein the said transversely exposed part of the insulative body is formed as rib projecting outwardly beyond the outer surfaces of the separated electrodes to provide a minimum conduction path length which is greater than the distance between the electrodes.

16. An electrode assembly according to claim 1, wherein, when the support structure and the electrodes are oriented generally in a horizontal direction, the tissue treatment and return electrodes are respectively downwardly and upwardly directed.

17. An electrode assembly according to claim 1, wherein the combination of the insulative body and the electrodes is supported solely by the said pair of conductors.

18. An electrode assembly according to claim 1, wherein the pair of conductors is formed as two spaced-apart insulatively-sleeved parallel support arms, and the combination of the insulative body and the electrodes forms a bridge between the arms at their distal ends.

19. An electrosurgical system comprising an electrosurgical instrument having an electrode assembly according to claim 1, and a radio frequency generator having at least a pair of output terminals for connection to the electrode assembly, wherein the generator is configured so as to apply a boosted power signal to the electrode assembly for an initial boost period upon activation of the electrode assembly to create a vapour layer over the active electrode.

20. A system according to claim 19, wherein the boost period has a duration of between 0.1 and 1 second.

21. A system according to claim 19, wherein the applied power is boosted by between 20% and 35% during the boost period.

22. An electrode assembly for the electrosurgical removal of tissue immersed in a electrically conductive liquid, wherein the assembly comprises at least first and second electrodes mounted on an insulator, and at least a pair of conductor wires forming an elongate support structure for housing in an endoscope, the combination of the electrodes and the insulator being secured to distal ends of the wires with one wire of the pair fixedly connected to the first electrode and the other wire of the pair fixedly connected to the second electrode, and wherein the electrodes comprise transversely extending metallic coverings mounted on oppositely directed surfaces of the insulator, the first electrode being mounted on a downwardly directed surface of the insulator and the second electrode being mounted on an upwardly directed surface of the insulator.

23. An electrode assembly according to claim 22, wherein the insulator forms a base member for the electrodes, the electrodes being mounted on the base member without adhesive.

24. An electrode assembly according to claim 22, wherein the insulator and the electrodes have interlocking shape features.

25. An electrode assembly according to claim 24, wherein the insulator has undercut grooves and the electrodes have complementary ribs which fit into the grooves and which are shaped to lock the electrodes to the insulator.

26. An electrode assembly according to claim 25, wherein the grooves in the insulator extend transversely, and the combination of the insulator and the electrodes is so configured that the electrodes are only insertable into the grooves from opposite respective sides of the insulator.

27. An electrode assembly according to claim 22, wherein the ratio of the exposed surface areas of the tissue treatment and return electrodes is greater than 1:1, the exposed surface areas being in respect of those surfaces of each electrode which are capable of being wetted when the assembly is immersed in liquid.

28. An electrode assembly according to claim 27, wherein the major part of the exposed surface of the tissue treatment electrode is rough, while that of the return electrode is smooth.

29. A method of electrosurgically removing tissue, comprising:

providing an electrode assembly having an elongate support structure which includes a pair of conductors and, mounted on a distal end of the support structure, a transversely extending insulator with a tissue treatment electrode secured on a lower face of the insulator and a return electrode secured on an oppositely directed upper face of the insulator, the electrodes being fixedly connected to respective conductors of the said pair, immersing the tissue to be treated in an electrically conductive liquid, bringing the electrode assembly to a location adjacent the tissue to be treated with the electrodes immersed in the conductive liquid, applying an electrosurgical radio frequency voltage between the electrodes of a sufficient magnitude to cause vaporisation of the conductive liquid at the tissue treatment electrode, applying the tissue treatment electrode to the surface of the tissue to be treated with the electrode assembly oriented such that the return electrode is directed away from the tissue surface, and reciprocating the electrode assembly generally in the lengthwise direction of the support structure to ablate the tissue by vaporisation thereof when contacted by the vapour layer over the tissue treatment electrode.

30. A method according to claim 29, wherein the ratio of the exposed surface area of the tissue treatment electrode to that of the return electrode is greater than 1:1, and wherein the electrosurgical ratio frequency voltage is applied to the electrode assembly from an electrosurgical generator having an open loop output impedance in the region of from 50 ohms to 250 ohms and is limited to a value in the range of from 250V peak to 600V peak.

31. A method according to claim 29, wherein the step of applying an electrosurgical radio frequency voltage includes firstly applying power to the electrode assembly at a boosted level during an initial boost period and then reducing the applied power.

32. A method according to claim 31, wherein the boost period has duration of between 0.1 and 1 second.

33. An electrode assembly for the electrosurgical removal of tissue immersed in an electrically conductive liquid, the assembly comprising an elongate support structure including a pair of conductor arms for carrying radio frequency electrosurgical currents, said conductor arms lying substantially in a common plane, an electrically insulative body mounted at a distal end of the support structure and extending transversely with respect to the support structure; a transversely extending conductive tissue treatment electrode secured to one side of the insulative body and electrically connected and fixedly secured to a first one of the conductor arms, and a transversely extending conductive return electrode secured to an opposite side of the insulative body and electrically connected and fixedly secured to a second one of the conductor arms, said insulative body, tissue treatment electrode, and return electrode, when secured together, forming a sandwich-like structure having an orientation that is substantially parallel to the plane in which the conductor arms lie.

* * * * *